US009296984B2

(12) United States Patent
Cimino et al.

(10) Patent No.: US 9,296,984 B2
(45) Date of Patent: Mar. 29, 2016

(54) TISSUE PROCESSING APPARATUS AND METHOD FOR PROCESSING ADIPOSE TISSUE

(71) Applicant: THE GID GROUP, INC., Louisville, CO (US)

(72) Inventors: William W. Cimino, Louisville, CO (US); Ramon Llull, Palma de Mallorca (ES); Adam J. Katz, Gainesville, FL (US)

(73) Assignee: THE GID GROUP, INC., Louisville, CO (US)

( * ) Notice: Subject to any disclaimer, the term of this patent is extended or adjusted under 35 U.S.C. 154(b) by 0 days.

(21) Appl. No.: 14/403,861

(22) PCT Filed: Sep. 5, 2013

(86) PCT No.: PCT/US2013/058292
§ 371 (c)(1),
(2) Date: Nov. 25, 2014

(87) PCT Pub. No.: WO2014/039697
PCT Pub. Date: Mar. 13, 2014

(65) Prior Publication Data
US 2015/0118752 A1    Apr. 30, 2015

Related U.S. Application Data

(60) Provisional application No. 61/697,716, filed on Sep. 6, 2012.

(51) Int. Cl.
C12M 1/33    (2006.01)
C12M 1/00    (2006.01)

(52) U.S. Cl.
CPC .............. *C12M 45/02* (2013.01); *C12M 47/04* (2013.01)

(58) Field of Classification Search
CPC .............................. C12M 45/02; C12M 47/04
See application file for complete search history.

(56) References Cited

U.S. PATENT DOCUMENTS 3,854,704 A    12/1974  Balas
4,438,032 A    3/1984   Golde et al.
(Continued)

FOREIGN PATENT DOCUMENTS

EP    0512769 A2    11/1992
JP    2009189282 A    8/2009
(Continued)

*Primary Examiner* — Leslie Deak
*Assistant Examiner* — Kai Weng
(74) *Attorney, Agent, or Firm* — Marsh Fischmann & Breyfogle LLP; Ross E. Breyfogle

(57) ABSTRACT

A portable apparatus useful for collection and processing of human biological material containing adipose, such as extracted during a lipoplasty procedure to prepare a concentrated product (e.g., stromal vascular fraction) or a fat graft composition. The apparatus has a container with a containment volume with a tissue retention volume and a filtrate volume separated by a filter and with a tapered portion to a collection volume for collecting concentrate product. Inlet and suction ports provide access to the tissue retention volume and filtrate volume, respectively, and an extraction port provides versatile access for removal of target processed concentrate material or fat graft material, which access may be via a lumen through a rotatable mixer shaft. Access ports may be configured for access only from above the container. The apparatus may include a tissue collector disposed in the disuse retention volume to engage and collect collagen or other stringy tissue. A method of processing adipose tissue to concentrate leuko stromal vascular cells includes multi-step processing using a portable container.

45 Claims, 21 Drawing Sheets

(56) References Cited

U.S. PATENT DOCUMENTS

| | | | |
|---|---|---|---|
| 4,820,626 A | 4/1989 | Williams et al. |
| 5,035,708 A | 7/1991 | Alchas et al. |
| 5,226,914 A | 7/1993 | Caplan et al. |
| 5,330,914 A | 7/1994 | Uhlen et al. |
| 5,336,616 A | 8/1994 | Livesey et al. |
| 5,372,945 A | 12/1994 | Alchas et al. |
| 5,409,833 A | 4/1995 | Hu et al. |
| 5,486,359 A | 1/1996 | Caplan et al. |
| 5,586,732 A | 12/1996 | Yamauchi et al. |
| 5,591,625 A | 1/1997 | Gerson et al. |
| 5,610,074 A | 3/1997 | Beritashvili et al. |
| 5,624,840 A | 4/1997 | Naughton et al. |
| 5,688,531 A | 11/1997 | Benayahu et al. |
| 5,728,739 A | 3/1998 | Ailhaud et al. |
| 5,736,396 A | 4/1998 | Bruder et al. |
| 5,786,207 A | 7/1998 | Katz et al. |
| 5,811,094 A | 9/1998 | Caplan et al. |
| 5,817,050 A | 10/1998 | Klein |
| 5,827,735 A | 10/1998 | Young et al. |
| 5,827,740 A | 10/1998 | Pittenger |
| 5,827,897 A | 10/1998 | Ailhaud et al. |
| 5,854,292 A | 12/1998 | Ailhaud et al. |
| 5,906,934 A | 5/1999 | Grande et al. |
| 5,908,784 A | 6/1999 | Johnstone et al. |
| 5,937,863 A | 8/1999 | Knowlton |
| 5,968,356 A | 10/1999 | Morsiani et al. |
| 6,200,606 B1 | 3/2001 | Peterson et al. |
| 6,261,549 B1 | 7/2001 | Fernandez et al. |
| 6,316,247 B1 | 11/2001 | Katz et al. |
| 6,391,297 B1 | 5/2002 | Halvorsen |
| 6,429,013 B1 | 8/2002 | Halvorsen et al. |
| 6,478,966 B2 | 11/2002 | Zhou et al. |
| 6,544,788 B2 | 4/2003 | Singh |
| 6,555,374 B1 | 4/2003 | Gimble et al. |
| 6,777,231 B1 | 8/2004 | Katz et al. |
| 6,841,150 B2 | 1/2005 | Halvorsen et al. |
| 6,852,533 B1 | 2/2005 | Rafii et al. |
| 7,001,746 B1 | 2/2006 | Halvorsen et al. |
| 7,033,587 B2 | 4/2006 | Halvorsen et al. |
| 7,078,230 B2 | 7/2006 | Wilkison et al. |
| 7,078,232 B2 | 7/2006 | Konkle et al. |
| 7,179,649 B2 | 2/2007 | Halvorsen |
| 7,266,457 B1 | 9/2007 | Hickman |
| 7,294,334 B1 | 11/2007 | Michal et al. |
| 7,361,368 B2 | 4/2008 | Claude et al. |
| 7,390,484 B2 | 6/2008 | Fraser et al. |
| 7,429,488 B2 | 9/2008 | Fraser et al. |
| 7,470,537 B2 | 12/2008 | Hedrick et al. |
| 7,473,420 B2 | 1/2009 | Fraser et al. |
| 7,501,115 B2 | 3/2009 | Fraser et al. |
| 7,514,075 B2 | 4/2009 | Hedrick et al. |
| 7,531,355 B2 | 5/2009 | Rodriguez et al. |
| 7,572,236 B2 | 8/2009 | Quick et al. |
| 7,582,292 B2 | 9/2009 | Wilkison et al. |
| 7,585,670 B2 | 9/2009 | Hedrick et al. |
| 7,595,043 B2 | 9/2009 | Hedrick et al. |
| 7,622,108 B2 | 11/2009 | Collins et al. |
| 7,641,643 B2 | 1/2010 | Michal et al. |
| 7,651,684 B2 | 1/2010 | Hedrick et al. |
| 7,659,118 B2 | 2/2010 | Furcht et al. |
| 7,670,596 B2 | 3/2010 | Collins et al. |
| 7,687,059 B2 | 3/2010 | Fraser et al. |
| 7,708,152 B2 | 5/2010 | Dorian et al. |
| 7,727,763 B2 | 6/2010 | McKenna, Jr. et al. |
| 7,732,190 B2 | 6/2010 | Michal et al. |
| 7,744,869 B2 | 6/2010 | Simon et al. |
| 7,749,741 B2 | 7/2010 | Bullen et al. |
| 7,771,716 B2 | 8/2010 | Hedrick et al. |
| 7,780,649 B2 | 8/2010 | Shippert |
| 7,780,860 B2 | 8/2010 | Higgins et al. |
| 7,789,872 B2 | 9/2010 | Shippert |
| 7,794,449 B2 | 9/2010 | Shippert |
| 7,887,795 B2 | 2/2011 | Fraser et al. |
| 7,901,672 B2 | 3/2011 | Fraser et al. |
| 2001/0030152 A1 * | 10/2001 | Wright ............... B01D 210/171 D35/6 |
| 2001/0033834 A1 | 10/2001 | Wilkison et al. |
| 2002/0076400 A1 | 6/2002 | Katz et al. |
| 2002/0119126 A1 | 8/2002 | Halvorsen |
| 2003/0082152 A1 | 5/2003 | Hedrick et al. |
| 2003/0161817 A1 | 8/2003 | Young et al. |
| 2003/0211602 A1 | 11/2003 | Atala |
| 2004/0067218 A1 | 4/2004 | Casteilla et al. |
| 2004/0097867 A1 | 5/2004 | Fraser et al. |
| 2004/0171146 A1 | 9/2004 | Katz et al. |
| 2005/0048034 A1 | 3/2005 | Fraser et al. |
| 2005/0076396 A1 | 4/2005 | Katz et al. |
| 2005/0153442 A1 | 7/2005 | Katz et al. |
| 2005/0282275 A1 | 12/2005 | Katz et al. |
| 2006/0051865 A1 | 3/2006 | Higgins et al. |
| 2007/0225665 A1 | 9/2007 | Perez-Cruet et al. |
| 2008/0014181 A1 | 1/2008 | Ariff et al. |
| 2008/0050275 A1 | 2/2008 | Bischof et al. |
| 2009/0042267 A1 * | 2/2009 | Park ............... B01F 7/00025 435/170 |
| 2010/0285521 A1 | 11/2010 | Vossman et al. |
| 2010/0285588 A1 | 11/2010 | Stubbers et al. |
| 2011/0117650 A1 | 5/2011 | Riordan |
| 2012/0003733 A1 | 1/2012 | Gueneron |
| 2012/0214659 A1 | 8/2012 | Do et al. |

FOREIGN PATENT DOCUMENTS

| | | |
|---|---|---|
| JP | 2011125813 A | 6/2011 |
| JP | 2013-507983 A | 3/2013 |
| WO | 2011052946 A2 | 5/2011 |
| WO | 2012006587 A2 | 1/2012 |
| WO | 2013106655 A1 | 7/2013 |

* cited by examiner

TISSUE PROCESSING APPARATUS AND METHOD FOR PROCESSING ADIPOSE TISSUE

CROSS REFERENCE TO RELATED APPLICATIONS

This patent application claims a benefit of U.S. Provisional Patent Application No. 61/697,716 titled "Tissue Processing Apparatus And Method For Processing Adipose Tissue", filed Sep. 6, 2012. This Application incorporates by reference the entire contents of each and every one of the following patent applications: U.S. Provisional Patent Application No. 61/697,716; International Patent Application No. PCT/US2013/021156, filed Jan. 11, 2013 and designating the U.S.; U.S. Provisional Patent Application No. 61/585,566 filed Jan. 11, 2012; International Patent Application No. PCT/US2011/043451, filed Jul. 8, 2011, which designated the U.S. and has entered the U.S. national phase as application Ser. No. 13/808,550; and U.S. Provisional Patent Application No. 61/363,150, filed Jul. 9, 2010.

FIELD OF THE INVENTION

The invention relates to apparatus related to collection and processing human biological material and methods of processing adipose tissue, for example to prepare a fat graft or a concentrate with leuko stromal vascular cells.

BACKGROUND OF THE INVENTION

Adipose tissue is recognized as a promising source of stem cells with at least multi-potent differentiation potential. Lipoasperate obtained during a lipoplasty procedure, such as lipo surgery, may be processed to prepare a so-called stromal vascular fraction (SVF) that is rich in leuko stromal vascular cells, which include stem cells. Processing to prepare SVF may include washing lipoasperate with saline solution, followed by enzymatic digestion of washed tissue using collagenase, and centrifuging digested material to prepare SVF in the form of a centrifuged pellet. Such collection and processing of tissue involves several steps with transfer of contents between different process containers for different tissue collection and processing steps, which is cumbersome and provides significant opportunities for error or contamination.

Some attempts have been made to design portable containers in which lipoaspirate may be collected and then processed within the container to digest tissue and prepare a concentrate rich in leuko stromal vascular cells. Potential benefits of using such portable containers include a reduced need to transfer material between containers to perform different process steps and a reduction in the need for multiple, specially-designed processing containers. However, such multi-step processing in portable containers faces significant equipment and process design and operating limitations, especially when attempting to process relatively large volumes of adipose tissue at one time. Desired leuko stromal vascular cells, including stem cells, are sensitive to processing conditions and viability of recovered cells may suffer significantly if processing is not adequately controlled. Also, recovery of cells from the container is of critical importance. Significant potential exists for loss of valuable cells to recovery from the container, such as by cells adhering to internal equipment and surfaces within the container. One problem with multi-step processing in a single portable container is that the container design and processing operations must accommodate the different requirements of each of the different process steps to be performed in the single container, and with severe volume constraints in relation to a practical size for such a portable container. In contrast, processing systems that involve transfer of contents between multiple different containers for performance of different process steps benefit from an ability to optimize equipment and process design for each process container that is dedicated to performance of a single step of an overall process. Therefore, multi-container processing has significant advantages in terms of step-by-step equipment and process optimization. Moreover, a multi-container design is better suited for automation, for example with automated transfer of processed material through conduits between different process containers or with automated control of process parameters for uniformity and process control.

SUMMARY OF THE INVENTION

Disclosed are portable apparatus, uses of such apparatus and methods for processing of human biological material, and which biological material may contain stringy tissue, such as is the case with adipose tissue. Stringy tissue such as collagen adds complexity to processing, for example due to potential plugging of filters and interference with separation of desired cellular components. Processing may include applications to prepare a washed or cleaned biological material or to release and prepare a concentrate of portions of a biological material feed. In the context of adipose tissue, processing may be directed to preparing washed tissue for a fat graft or to prepare a concentrate product rich in leuko stromal vascular cells. Leuko stromal vascular cells may be referred to herein also as stromal vascular cells or stromal vascular fraction cells.

Obtaining a high recovery in a concentrate of viable leuko stromal vascular cells from adipose tissue and effective removal of such concentrate material of such a concentrate from the container in an operationally convenient manner have been significant challenges for multi-step processing in a single container. Also challenging has been providing a portable container apparatus design that provides versatility in being adaptable both for applications involving preparation of washed adipose tissue for fat grafts and for applications involving digestion of adipose tissue and release and concentration of leuko stromal vascular cells. The presence of stringy tissue components, such as collagen, in adipose tissue complicates processing, and especially in the context of separating leuko stromal vascular cells for recovery in a concentrate at a high yield in a high quality concentrate product from a multi-step processing container. Also even after preparation of such a cell concentrate in a multi-step processing container, removal of the cell concentrate material from the container is complicated by the presence of other materials that may remain in the container after preparation of the cell concentrate and possible physical loss of leuko stromal vascular cells through adherence of cells to exposed surfaces within the container (e.g., surfaces of container walls, filters, mixers or other apparatus components disposed in the container).

A first aspect of the disclosure is provided by an apparatus for processing human biological material containing stringy tissue. The stringy tissue may comprise collagen and/or other stringy tissue components, for example as is typically the case with lipoaspirate. The apparatus includes a tissue collector disposed in a tissue retention volume of a container. The presence of stringy tissue presents a significant problem in relation to recovery of leuko stromal vascular cells from lipoaspirate, especially when processing large tissue volumes through multiple processing steps in a single container. Such stringy tissue may tend to collect on and clog a filter through which stromal vascular cells pass for collection. Problems with stringy tissue may be reduced to some degree by using a pre-filter upstream of the container to filter out stringy tissue before introduction into the container. However, such pre-filters are not easy to use and introduce additional complexity for the medical professional performing a lipoplasty operation. Also, even with the use of such a pre-filter, some stringy tissue may still be introduced into the container and may significantly impact cell collection in the container. The inclusion of a tissue collector in the container may significantly reduce or even in some cases eliminate the need and complexity of using a separate pre-filter to remove some or all of the stringy tissue prior to introduction of tissue into the container for processing.

The apparatus of the first aspect includes a container having an internal containment volume, the internal containment volume including a tissue retention volume and a filtrate volume. A filter is disposed within the internal containment volume with the tissue retention volume on one side of the filter and the filtrate volume on another side of the filter with the tissue retention volume and the filtrate volume being in fluid communication through the filter. An inlet port in fluid communication with the tissue retention volume is configured to access the tissue retention volume for introducing human biological material into the tissue retention volume. A suction port in fluid communication with the filtrate volume is configured to access the filtrate volume for suctioning material from the filtrate volume. A tissue collector is disposed in the tissue retention volume and rotatable relative to the container in at least a first direction of rotation about an axis of rotation. The tissue collector may include at least one toothed member that sweeps through a portion of the tissue retention volume when the tissue collector is rotated in the first direction. The toothed member may be configured with a plurality of teeth to collect and retain stringy tissue when the tissue collector is rotated in the first direction in contact with human biological material containing the stringy tissue disposed in the tissue retention volume.

A number of feature refinements and additional features are applicable to the apparatus of the first aspect. These feature refinements and additional features may be used individually or in any combination. As such, each of the following features may be, but are not required to be, used with any other feature or combination of the first aspect or any other aspect of the disclosure.

Each such toothed member may include at least 3, at least 4 or at least 5 teeth and may include an open space between the teeth of each pair of adjacent said teeth. Each such toothed member may include up to 10, up to 20 or up to 25 or more such teeth. A leading edge of a toothed member may be made up with at least 10 percent, at least 20 percent, at least 30 percent, at least 40 percent, at least 50 percent, at least 60 percent or more of open spaces. Such a leading edge of a toothed member may be made up of no more than 99 percent, 90 percent, 80 percent, 70 percent, 60 percent or 50 percent of teeth. By space on a leading edge of a toothed member made up of such open spaces, it is meant the space between tops of the teeth, and likewise the space on a leading edge made up of a toothed member refers to the space along the edge occupied by the tops of the teeth.

The tissue collector may include at least 1, at least 2, at least 3 or at least 5 such toothed members. The tissue collector may include up to 6, up to 10 or even more such toothed members. When the tissue collector includes multiple toothed members, some or all of such toothed members may have the same or a different configuration, for example in relation to member size, tooth design, number of teeth, teeth density, or other design features.

The apparatus may include at least 1 or at least 2 or more of such tissue collectors. The apparatus of the first aspect may include only 1, up to 2 or more such tissue collectors when the apparatus includes a plurality of tissue collectors two or more of the tissue collectors may be of the same configuration or of different configurations.

A toothed member may have a first end located radially toward the axis of rotation and a second end located radially away from the axis. Such a second end may be located a distance from the axis of at least 1 centimeter, at least 2 centimeters, at least 3 centimeters or at least 5 centimeters or more from the axis. Such second end may be located a distance from the axis of up to 6 centimeters, up to 8 centimeters, up to 10 centimeters or more from the axis.

Teeth may project toward a leading side, or edge, of the toothed member when the tissue collector is rotated in the first direction. Teeth may project in a plane of rotation of the toothed member when the tissue collector is rotated in the first direction. Teeth may have a height in a range having a lower limit of 1 millimeter, 2 millimeters, 3 millimeters or 5 millimeters and an upper limit of 20 millimeters, 15 millimeters or 10 millimeters relative to a bottom of an adjacent open space.

The apparatus of the first aspect may have one or more than one mixing impeller in the tissue retention volume. A mixing impeller may be configured to direct axial flow from the mixing impeller in a direction toward the tissue collector. Such a mixing impeller may include at least one portion configured to scrape a portion of the filter when the mixing impeller is operated. Each such portion of a mixing impeller configured to scrape a portion of the filter may include a peripheral edge portion of an impeller blade. At least a part of each such portion of the filter may be in a tapered portion of the filter that is disposed in a tapered portion of the internal containment volume. The tissue collector and such a mixing impeller may be coaxial and rotatable about a common axis of rotation. A spacing along such an axis between such a mixing impeller and a toothed member of the tissue collector may be at least 0.25 centimeter, at least 0.5 centimeter, at least 1 centimeter or at least 2 centimeters. A spacing along the axis between such a mixing impeller and a toothed member of the tissue collector may be up to 3 centimeters, up to 5 centimeters or even more. Such a mixing impeller may extend to a first radial distance from the axis and the tissue collector may extend to a second radial distance from the axis, with the second radial distance being larger than the first radial distance. Such a second radial distance may be at least 1 millimeter, at least 2 millimeters or at least 3 millimeters larger than such a first radial distance. Such a second radial distance may be no more than 3 centimeters, no more than 2 centimeters or no more than 1 centimeter larger than such a first radial distance.

In addition to such a mixing impeller, which may be a first mixing impeller, the apparatus of the first aspect may include one or more additional mixing impellers disposed in the tissue retention volume. The apparatus of the first aspect may include a second mixing impeller configured to direct axial flow in a direction away from the tissue collector when the rotatable shaft is rotated in the first direction. The tissue collector and such a second mixing impeller may be coaxial and rotatable about a common axis in the first direction. A spacing along an axis between such a second mixing impeller and a toothed member of the tissue collector may be at least 0.25 centimeter, at least 0.5 centimeter, at least 1 centimeter or at least 2 centimeters. A spacing along an axis between such a second mixing impeller and a toothed member of the tissue collector may be up to 3 centimeters, up to 5 centimeters or even more. Such a second mixing impeller may extend to a third radial distance from an axis that is at least 1 millimeter, at least 2 millimeters or at least 3 millimeters smaller than a radial distance from the axis to which the tissue collector may extend. Such a third radial distance may be no more than 3 centimeters, no more than 2 centimeters or no more than 1 centimeter larger than a radial distance to which the tissue collector may extend.

The apparatus of the first aspect may be orientable in a first orientation in which the inlet port and the suction port are configured for access therethrough from above the container into the internal containment volume. The apparatus of the first aspect may be configured to have all access to the internal containment volume be from above the container in the first orientation.

The apparatus of the first aspect may include an extraction port configured for accessing the internal containment volume to remove processed biological material from the internal containment volume. Such an extraction port may be configured for access therethrough from above the container into the internal containment volume when the apparatus is oriented in a first orientation. Access through such an extraction port may be through a lumen extending through a rotatable shaft aligned with the axis. In an alternative configuration, no access may be provided into the internal containment volume through a lumen extending through a rotatable shaft. A permanent obstruction may be placed in such a lumen to prevent such access. The apparatus may be configured for use to prepare a fat transfer, or fat graft, when such a permanent obstruction is placed in such lumen through a rotatable shaft. Such a permanent obstruction may be in the form of solder or a weld or a permanent plug. As an alternative, a solid mixer shaft may be used instead of an obstruction in a lumen. Processed tissue in the tissue retention volume, for example washed adipose tissue for use in a fat graft, may be removed from the tissue retention volume from an auxiliary, or additional access, port provided into the tissue retention volume. Such an additional access port may provide access through a top of the container into the tissue retention volume. To remove processed tissue from the tissue retentive volume adipose tissue, a syringe may be inserted into or mated with the additional access port and the apparatus tipped to cause processed tissue in the tissue retention volume to collect in the vicinity of the additional access port to be withdrawn into the syringe. As an alternative processed tissue in the tissue retention volume may be removed through the inlet port, which may be in a similar manner as described for such an additional access port.

The filter may have a separation size of at least 70 microns, at least 100 microns, at least 150 microns, at least 175 microns or at least 200 microns. The filter may have a separation size of no larger than 800 microns, no larger than 700 microns, no larger than 600 microns, no larger than 500 microns, no larger than 475 microns, no larger than 450 microns, no larger than 425 microns, no larger than 400 microns, no larger than 350 microns, no larger than 300 microns or no larger than 250 microns. For some applications, the filter may have a separation size that is larger than 400 microns, for example for cell processing applications when the apparatus of the first aspect is to be used to a recover a stromal vascular fraction concentrate from adipose tissue. Even though stromal vascular cells will easily pass through a 200 micron filter, the larger filter size may be advantageous to promote recovery of most or substantially all of the stromal vascular cells in the filtrate volume. Smaller size filters may plug to a degree that significantly reduces cell yield in terms of cell collection in and recovery from the filtrate volume. In some other applications, the filter may have a separation size of 400 microns or less, for example for processing adipose tissue for use in a fat graft, or fat transfer, operation. The filter may not be as susceptible to clogging in those applications and a smaller filter size permits retention of desired adipose tissue in the tissue retention volume. By separation size, it is meant the size at which the filter effects separation between particles passing through and particles rejected by the filter during normal operation. The separation size may be determined by the size of openings provided in a surface filter, such as the mesh size of a mesh bag filter or of a rigid mesh screen filter.

The apparatus of the first aspect may be configured to be received in a centrifuge for centrifuging the container.

The apparatus of the first aspect may comprise human biological tissue comprising stringy tissue disposed in the tissue retention volume in contact with the toothed member. The stringy tissue may comprise collagen. Tissue to be processed in the apparatus of the first aspect may comprise adipose removed from a patient during a lipoplasty procedure (e.g., lipoaspirate). For example, the term tissue may be used herein to refer to in-tact tissue, disrupted tissue, tissue fragments and biological fluids associated with or separate from tissue. The apparatus may be orientable in a collection orientation for collection of human biological material, or tissue, such as may comprise adipose tissue collected during a lipoplasty procedure. The collection orientation is also referred to herein as an access orientation or a first orientation, and the terms are used interchangeably. For convenience of description except as noted, the apparatus is described as oriented in such a collection orientation. As such, relational references such as to top, bottom, up, down, above, below, elevations, vertical, horizontal and the like are in relation to the apparatus as oriented in the collection orientation. The apparatus may be configured such that the apparatus may be stably supported in the collection orientation. For example, the apparatus may have a base configured for interfacing with a flat, substantially horizontal surface (e.g., counter top or table top) to stably support the apparatus in the collection orientation, or may be held in a mounting structure that maintains the apparatus in the collection orientation. Although such an orientation is referred to as a "collection" orientation it should be appreciated that use of the apparatus is not limited to being oriented only in the collection orientation or that only human biological material collection may be performed while the apparatus is oriented in the collection orientation. The apparatus may be advantageously configured to permit performance of many different operations with the apparatus when the apparatus is oriented in the collection orientation.

The apparatus of the first aspect may be used in a variety of processing applications. The apparatus may, for example, be used for preparation of concentrated or separated portions of the collected human biological material, for example to produce a stromal vascular fraction rich in leuko stromal vascular cells, including stem cells, derived from adipose tissue. As another example, the apparatus may be used for preparation of a fat graft comprising adipose. The apparatus has a design that accommodates retention of a target material (e.g., leuko stromal vascular cells or adipose) in a single container from collection through preparation of a desired product containing the target material. By target material, it is meant some component or components from or some portion or portions of collected human biological material of interest for recovery following processing in the apparatus, such as recovery in a concentrated or modified form relative to the collected human biological material (e.g., stromal vascular fraction concentrate rich in stem cells and other leuko stromal vascular cells, cleaned adipose-containing fraction for fat grafting applications).

The apparatus of the first aspect may be used during multiple processing steps to prepare, for example, a stromal vascular fraction concentrate (e.g., concentrate rich in leuko stromal vascular cells) from human biological material comprising adipose or a fat graft containing adipose, without the need to transfer a target material being processed between different containers for different processing steps. The apparatus may be used initially to collect the human biological material (e.g. tissue and fluids) during a lipoplasty procedure or other tissue extraction procedure, or tissue that has already been extracted in another procedure may be introduced into the apparatus for processing. The apparatus, and therefore also the container of the apparatus, may be portable and easily transportable between locations where collection or different processing operations may be conducted.

The apparatus of the first aspect may have a collection volume within the filtrate volume (i.e., is a part of the filtrate volume). The collection volume may have a bottom elevation corresponding to a bottom elevation of the filtrate volume. The collection volume may have a top elevation that is lower than a bottom elevation of the tissue retention volume.

The apparatus of the first aspect may include an extraction port in fluid communication with the internal containment volume and configured for removing processed biological material from the internal containment volume. Any or all of the inlet port, the suction port and the extraction port may be configured for access therethrough from above the container into the internal containment volume. The extraction port may be located above a portion of the filter, so that the advancing tip of a hypodermic needle pierces the filter when the tip of the hypodermic needle is advanced from the extraction port into the collection volume. The collection volume may include a nadir and the extraction port may be positioned above the nadir so that the tip of a hypodermic needle inserted through the extraction port may be advanced vertically downward to the vicinity of the nadir of the collection volume.

The apparatus of the first aspect may be configured for advancing a hypodermic needle through a lumen and out of the distal end of the lumen to access the collection volume with an advancing tip of the hypodermic needle. The distal end of the lumen may be located in the tissue retention volume above a portion of the filter, so that the advancing tip of the hypodermic needle may pierce and pass through the filter when the tip of the hypodermic needle exits the distal end of the lumen and is advanced from the distal end of the lumen into the collection volume. The collection volume may include a nadir, and an axis of the lumen may be aligned so that the tip of a hypodermic needle exiting the distal end of the lumen may be advanced to the vicinity of the nadir of the collection volume. The hypodermic needle may thus access the collection volume to permit injection of material into and/or aspiration of material from the collection volume (e.g., aspiration of stromal vascular fraction concentrate or other processed biological material collecting in the collection volume during processing).

The apparatus of the first aspect may be designed for single-use, and piercing the filter with a hypodermic needle may beneficially provide a safety mechanism for preventing reuse, and risks associated therewith, by damaging the filter in a way that renders the filter unsatisfactory for reuse.

As noted, the suction port is in fluid communication with the filtrate volume. By the suction port being in fluid communication with the filtrate volume, it is meant that the suction port is fluidly connected directly to the filtrate volume, and not indirectly through the tissue retention volume and the filter. The fluid communication may be provided by a dedicated conduit extending from the suction port to a desired location within the filtrate volume where it is desired to apply suction directly to the filtrate volume. The suction port may be in fluid communication with a tapered portion of the internal containment volume through a conduit providing fluid communication from the suction port to a location within the filtrate volume that is also within the tapered portion of the internal containment volume. The conduit may extend through the filtrate volume from adjacent the suction port to such a location within the filtrate volume. The suction port may be located above the tapered portion of the internal containment volume. The suction port may be configured for access through the suction port from above the container. The suction port may be configured for connection to a vacuum system to suction material from the filtrate volume, such as material that passes through the filter from the tissue retention volume to the filtrate volume.

The apparatus of the first aspect may include multiple suction ports. For example, the apparatus may include a first suction port as described in the preceding paragraph that is in fluid communication with a first location in the filtrate volume within the tapered portion of the internal containment volume through a first conduit, and the apparatus may include a second suction port through which components passing through the filter from the tissue retention volume to the filtrate volume may be suctioned from the filtrate volume through a second conduit extending from the second suction port to a second location within the filtrate volume. The second conduit may be configured to permit adjustment of the elevation of the second location within the filtrate volume.

Any one or more of the inlet port, the suction port of other ports providing access to the internal containment volume may be configured for access through the port from above. In this way, access through each such port may be conveniently from above the apparatus, providing a significant advantage to a user of the apparatus in that such a user may focus all access manipulations from above the apparatus while the apparatus is in a normal position in the collective orientation, for example with the apparatus freestanding on a flat work surface such as a table or counter. Although such access from above the container may be at some angle relative to vertical, in a preferred implementation the access through such port is in a vertical direction from above the container. In one preferred implementation, all access to the internal containment volume may be through access ports wherein each such access port (e.g., inlet port, suction port, extraction port, other ports) is configured for access through the access port only from above the container. In another preferred implementation, all access ports may be configured for access through each such access port in a vertical direction from above the container.

The internal containment volume of the container may have a tapered portion that tapers in a downward direction. The tapered portion may have a cross-sectional area that tapers, or reduces in size, in a direction toward the bottom of a collection volume. The tapered portion of the internal containment volume may help to direct and concentrate target dense material (e.g., dense cells, stromal vascular fraction) toward and into the collection volume. At least a portion of the collection volume may be located within or below such a tapered portion. At least a part of the tapered portion may be located above the collection volume. The tapered portion of the internal containment volume may have a conical shape or any other shape with a cross-sectional area that tapers to reduce in size in a direction toward the bottom of the collection volume. In various implementations, at least a part of the tapered portion may be located above the collection volume. The tapered portion may have a uniform taper geometry (e.g., constant rate of taper) or may have a varying taper geometry (e.g., varying rate of taper in the direction of the taper).

In some implementations, the internal containment volume may have at least a first tapered portion and a second tapered portion that is located vertically lower than the first tapered portion, wherein the first tapered portion has a greater rate of taper than the second tapered portion. The first tapered portion may be defined at least in part by a first internal wall surface of the container that is at a first angle relative to horizontal when the apparatus is in an access orientation in a range having a lower limit of 20°, 25°, 30°, 35°, 40°, or 45° and an upper limit of 65°, 60°, 55°, or 50° and the second tapered portion may be defined at least in part by a second internal wall surface of the container that is at a second angle relative to horizontal when the apparatus is in an access orientation in a range having a lower limit of 50°, 60°, 65° or 70° and an upper limit of 89°, 88°, 85° or 82°, provided that the second angle is larger than the first angle. Such a first tapered portion, for example as viewed in a vertical plane cross-section, may be defined at least in part by opposing ones of such first internal wall surfaces. Such a second tapered portion in such a vertical cross-section may be defined at least in part by opposing ones of such second internal wall surfaces. The second tapered portion may be disposed partially or entirely within the filtrate volume. The second tapered portion may include at least a portion of a collection volume within the filtrate volume or may be entirely within such a collection volume. The second tapered portion may be or may be a part of a pellet well located in a bottom portion of such a collection volume. The volume within the second tapered portion of the internal containment volume may be in a range having a lower limit of from 0.2 percent, 0.3 percent, 0.5 percent, 0.7 percent or 0.8 percent of the portion of available processing volume of the container that is within the tissue retention volume and an upper limit of 2.5 percent, 2 percent, 1.5 percent, 1.2 percent or 1.1 percent of the portion of such available processing volume of the container that is within the tissue retention volume. Such a portion of the available processing volume within the tissue retention volume may be a volume capacity of the apparatus for human biological material feed (e.g., adipose tissue feed) that may be processed in the apparatus. For some implementations, the second tapered portion of the internal containment volume may have a volume in a range having a lower limit of 0.3 cubic centimeter, 0.5 cubic centimeter, 0.7 cubic centimeter, 0.8 cubic centimeter, 0.9 cubic centimeter or 1.0 cubic centimeter and an upper limit of 5 cubic centimeters, 3 cubic centimeters, 2 cubic centimeters, 1.5 cubic centimeters, or 1.3 cubic centimeters. The second tapered portion may have a vertical dimension when the apparatus is in an access orientation of at least 1 centimeter, at least 1.5 centimeters, at least 2 centimeters or at least 2.5 centimeters. The second tapered portion may have a vertical height dimension when the apparatus is in an access orientation of up to 10 centimeters, up to 5 centimeters, up to 4 centimeters or up to 3 centimeters. The internal containment volume may include a third tapered portion that is located below the second tapered portion that has a greater rate of taper than the second tapered portion. A third tapered portion may be defined at least in part by a third internal wall surface of the container that is at an angle relative to horizontal that is smaller than the second angle. The third angle may have a value as described previously for the first angle, provided that the second angle is larger than the third angle. The third tapered portion may occupy the lowermost portion of a collection volume in the filtrate volume, which may be a lowermost portion in a pellet well. The third tapered portion may have a vertical height dimension when the apparatus is in an access orientation that is smaller than a vertical height dimension of the second tapered portion. The third tapered portion may have such a vertical height dimension that is not larger than 1 centimeter or no larger than 0.5 centimeter. The third tapered portion may have a volume that is smaller than the volume of the second tapered portion. The third tapered portion may have a volume that is no larger than 0.5 cubic centimeter, no larger than 0.3 cubic centimeter or no larger than 0.2 cubic centimeter. The first tapered portion may have a vertical height dimension below a bottom of the filter that is smaller than a vertical height dimension of the second tapered portion, and such a vertical height dimension of the first tapered portion may be at least 0.5 centimeter or at least 1 centimeter. The first tapered portion may beneficially help stromal vascular fraction materials to move into the second tapered portion when the apparatus is centrifuged. The second tapered portion, and also the third tapered portion if present, may be or be part of a pellet well, as discussed below.

Surprisingly, it has been found that the material of a pellet phase containing a concentrate of leuko stromal vascular cells from adipose tissue, such as may be formed during centrifuging, may be directly aspirated from a collection volume at the bottom of the filtrate volume without first removing overlying less-dense material phases and without dispersing the material of the pellet phase in a suspension liquid. Although the pellet phase may typically have a very high viscosity, it has been found that it is possible to aspirate the pellet phase material, for example though a hypodermic needle, without first diluting the pellet phase material to reduce viscosity, and without detrimental breakthrough of overlying, low viscosity aqueous liquid phase during the aspiration. This permits significant simplification in processing to remove such pellet phase material in some implementations.

The internal containment volume of the apparatus of the first aspect may include a pellet well that may help facilitate effective removal of pellet phase material by direct aspiration. The pellet well may be disposed in a bottom portion of the filtrate volume below a bottom elevation of the filter and accessible only from above when the apparatus is in an access orientation. Such a pellet well that may be configured as a relatively deep, narrow chamber to help facilitate effective direct aspiration of pellet phase material, such as a concentrate of leuko stromal vascular cells.

A pellet well may include a second tapered portion, and also optionally a third tapered portion, of the internal containment volume below a first tapered portion, as described above.

The filtrate volume may include a lower tapered portion below a bottom elevation of the filter and above a top elevation of a pellet well. The lower tapered portion of the filtrate volume may be defined by internal wall surfaces of the container that are each inclined relative to horizontal at a maximum angle of no larger than 60° when the container is in an access orientation. The lower tapered portion of the filtrate volume may be or include that portion of a first tapered portion of the internal containment volume, as discussed above, that is located below the filter. At least a portion of the pellet well may be defined by a wall surface of the container inclined relative to horizontal at an angle that is larger than the maximum angle when the apparatus is in the access orientation. The wall surface of the container defining at least a portion of the pellet well may be inclined relative to horizontal at an angle of at least 70°, at least 75°, at least 80°, or at least 85°. The wall surface of the container defining at least a portion of the pellet well may be inclined relative to horizontal at an angle of 90° (vertical) or less than 90°, when the apparatus is in the access orientation.

A pellet well may have a volume in a range having a lower limit of 0.3 cubic centimeter, 0.5 cubic centimeter, 0.7 cubic centimeter, 0.8 cubic centimeter, 0.9 cubic centimeter or 1.0 cubic centimeter and an upper limit of 5 cubic centimeters, 3 cubic centimeters, 2 cubic centimeters, 1.5 cubic centimeters, or 1.3 cubic centimeters.

A pellet well may have a vertical height dimension when the apparatus is in an access orientation of at least 1 centimeter, at least 1.5 centimeters, at least 2 centimeters or at least 2.5 centimeters. A pellet well may have a vertical height dimension when the apparatus is in an access orientation of up to 10 centimeters, up to 5 centimeters, up to 4 centimeters or up to 3 centimeters.

A pellet well may have at least one portion with a vertical length of 1 centimeter, a maximum horizontal dimension along the vertical length of no larger than 5 millimeters and a minimum horizontal dimension along the vertical length of no smaller than 1.5 millimeters. Having at least one such a portion may facilitate receiving a distal end of a hypodermic needle or other aspiration tube in a relatively deep, narrow volume for aspiration of pellet phase material without significant premature breakthrough of less-dense aqueous liquid phase that may be disposed above the pellet phase following centrifuging.

A tapered portion of the internal containment volume may have a tapered portion nadir corresponding with a bottom elevation of the internal containment volume. The bottom elevation of a collection volume may correspond with the bottom elevation of the internal containment volume. Wall surfaces of the container defining a tapered portion of the internal containment volume may coverage at a point at the tapered portion nadir. This is a particularly beneficial configuration, especially for applications when target material is to be collected in and removed from the collection volume in the vicinity of the tapered portion nadir. Such a tapered portion nadir may be located in a pellet well located at the bottom of a collection volume.

The apparatus of the first aspect may be configured with a very convenient size from a number of perspectives, and with efficient use of the internal containment volume to facilitate efficient collection of biological material and versatility in post-collection processing. The apparatus may be sized for convenient hand transportation, such as between a location where human biological material may be collected to other, different locations, where various processing of collected material may be carried out. The apparatus may also be sized for convenient manipulation by a person.

For many applications, the apparatus of the first aspect may be sized and configured such that the internal containment volume has a volume in a range with a lower limit of 100 cubic centimeters, 200 cubic centimeters, 250 cubic centimeters, 300 cubic centimeters, 500 cubic centimeters, 600 cubic centimeters or 700 cubic centimeters and an upper limit of 1500 cubic centimeters, 1300 cubic centimeters, 1100 cubic centimeters, 1000 cubic centimeters, 900 cubic centimeters, 800 cubic centimeters, 500 cubic centimeters, 400 cubic centimeters or 300 cubic centimeters, provided that the upper limit is larger than the lower limit. One preferred range for many applications is for the internal containment volume to be in a range of 700 cubic centimeters to 1000 cubic centimeters. Another preferred range for some applications is for the internal containment volume to be within a range of from 100 cubic centimeters to 400 cubic centimeters, such as for example to prepare a concentrate of leuko stromal vascular cells for administration to the vicinity of a joint for treatment of osteoarthritis By internal containment volume, it is meant the total internal volume contained within the walls defining the container, including volume that is occupied by internal hardware, such as for example may be occupied by a mixing device, barrier member, suction conduits, barrier skirt, etc. As will be appreciated, less than all of the internal containment volume will be available for processing within the internal containment volume.

The terms "available processing volume" or "useful volume" are used interchangeably herein to refer to the portion of the internal containment volume that is effectively available to receive and process human biological material and additives (e.g. wash other additives) during use of the apparatus of the first aspect for collection of biological material or for post-collection processing. This available processing volume is equal to the internal containment volume less portions of the internal containment volume occupied by hardware (e.g., mixing device, filter, skirt, suction tubes, barrier member, etc) and less unoccupied portions of the internal containment volume not effectively accessible for occupation by biological material during collection operations or by biological material or additives during post-collection processing. For example, the available processing volume may exclude a small volume at the top of the container that is above a bottom extension of the inlet port into the internal containment volume. This small void space may be beneficial to permit space for fluid to slosh within the container when contents of the container may be internally mixed or externally agitated (e.g., by a shaker table). For many applications, the available processing volume may be in a range having a lower limit of 75 cubic centimeters, 100 cubic centimeters, 200 cubic centimeters, 300 cubic centimeters, 400 cubic centimeters, 500 cubic centimeters, 600 cubic centimeters, 650 cubic centimeters or 700 cubic centimeters and an upper limit of 1300 cubic centimeters, 1100 cubic centimeters, 1000 cubic centimeters, 900 cubic centimeters, 850 cubic centimeters, 800 cubic centimeters, 750 cubic centimeters, 600 cubic centimeters, 500 cubic centimeters, 400 cubic centimeters or 300 cubic centimeters, provided that the upper limit is larger than the lower limit. In one preferred implementation for many applications, the available processing volume may be in a range of from 700 cubic centimeters to 850 cubic centimeters.

Advantageously, the apparatus of the first aspect may be configured so that a large portion of the available processing volume is within the tissue retention volume, while still permitting a high level of performance for various processing operations. The tissue retention volume may comprise at least 60 percent, at least 65 percent or at least 70 percent of the available processing volume with the container. Often, the tissue retention volume will comprise not more than 95 percent, not more than 90 percent or not more than 85 percent of the available processing volume. For many preferred implementations, the tissue retention volume may comprise a portion of the available processing volume that is at least 50 cubic centimeters, at least 100 cubic centimeters, at least 200 cubic centimeters, at least 300 cubic centimeters, at least 400 cubic centimeters, at least 500 cubic centimeters, at least 600 centimeters or at least 650 cubic centimeters. The apparatus may advantageously be configured with only a small portion of the available processing volume occupied by a collection volume, located below the filter. For example, the collection volume may comprise no more than 10 percent, no more than 7 percent or no more than 5 percent of the available processing volume.

For many preferred implementations the apparatus may have a collection volume that is no larger than 75 cubic centimeters, no larger than 50 cubic centimeters, no larger than 30 cubic centimeters, no larger than 20 cubic centimeters, no larger than 10 cubic centimeters or no larger than 5 cubic centimeters. The collection volume may be at least 1 cubic centimeter, at least 2 cubic centimeters, or at least 4 cubic centimeters. In one preferred implementation, the collection volume may be in a range of from 10 cubic centimeters to 30 cubic centimeters. For other implementations, the collection volume may be smaller than 10 cubic centimeters. Typically, the entire collection volume will make up part of the available processing volume.

One significant area of medical application for use of the apparatus of the first aspect is to prepare leuko stromal vascular cell concentrate for use in the treatment of osteoarthritis, for example in the vicinity of a patient's joint. In some applications for treatment of osteoarthritis, the apparatus may be configured with a relatively small internal containment volume designed to process a volume of adipose tissue to prepare a volume of leuko stromal vascular cells that may be appropriate for use in a single injection formulation for treatment of osteoarthritis at a joint. In some implementations, the apparatus may have an internal containment volume with a volume in a range having a lower limit of 150 cubic centimeters, 200 cubic centimeters or 250 cubic centimeters and an upper limit of 400 cubic centimeters, 350 cubic centimeters or 300 cubic centimeters. The apparatus may be designed with a tissue retention volume that includes a portion of the available processing volume of the apparatus in a range having a lower limit of 50 cubic centimeters, 75 cubic centimeters or 100 cubic centimeters and an upper limit of 250 cubic centimeters, 200 cubic centimeters 150 cubic centimeters or 125 cubic centimeters. The apparatus may be designed to collect a pellet phase volume, which may correspond with a pellet well volume, in a range of from 0.5 cubic centimeter, 0.75 cubic centimeter or 1 cubic centimeter and an upper limit of 2.5 cubic centimeters, 2 cubic centimeters 1.5 cubic centimeters or 1.3 cubic centimeters.

The apparatus of the first aspect may be packaged within a hermetic enclosure, for example as packaged for transportation and storage prior to use. The apparatus may be sterilized prior to packaging and maintained in a sterile environment within the hermetic enclosure at least until the apparatus is removed from the hermetic enclosure for use. The apparatus may be designed for a single use following removal from the hermetic enclosure. After such single use, the apparatus may be disposed of in an appropriate manner.

A second aspect of the disclosure is provided by an apparatus for processing human biological material including a container having an internal containment volume, the internal containment volume including a tissue retention volume and a filtrate volume. A filter is disposed within the internal containment volume with the tissue retention volume on one side of the filter and the filtrate volume on another side of the filter with the tissue retention volume and the filtrate volume being in fluid communication through the filter. An inlet port in fluid communication with the tissue retention volume is configured to access the tissue retention volume for introducing human biological material into the tissue retention volume. A suction port in fluid communication with the filtrate volume is configured to access the filtrate volume for suctioning material from the filtrate volume. The filtrate volume includes a pellet well in a collection volume located below a bottom elevation of the filter.

A number of feature refinements and additional features are applicable to the apparatus of the second aspect. These feature refinements and additional features may be used individually or in any combination. As such, each of the following features may be, but are not required to be, used with any other feature or combination of the second aspect or any other aspect of the disclosure.

The apparatus of the second aspect may be or include any feature or a combination of any features described with respect to the first aspect. The pellet well of the apparatus of the second aspect may be or have any feature or features described with respect to a pellet well for the apparatus of the first aspect. The apparatus of the second aspect may have a design that does not include a tissue collector as described with respect to the first aspect.

A third aspect of the disclosure is provided by a method of processing adipose tissue to concentrate leuko stromal vascular cells associated with the adipose tissue. The method combines particular processing in combination with a portable container of an apparatus for processing human biological material containing stringy tissue, to address significant design constraints associated with the use of portable containers for multi-step processing of adipose tissue. The method of the third aspect includes multi-step processing within a portable container having a filter inside the container. The multi-step processing includes washing the adipose tissue within the container to remove contaminants from the adipose tissue. After the washing, the method includes digesting adipose tissue within the container, comprising adding to the container a volume of enzyme-containing digestion medium to contact washed adipose tissue in the container. After permitting enzymatic digestion in the container for a retention time following adding the digestion medium, the method includes disposing the container in a centrifuge and centrifuging the container in the centrifuge to form density-separated phases within the container, the density-separated phases including lower-density material phases and a higher-density pellet phase comprising leuko stromal vascular cells. After the centrifuging, the method includes selectively removing material of the pellet phase from the container.

The method particularly addresses processing within the constrained context of multiple-step processing within a single portable container. The method may permit effective processing within such a portable container in a manner to address inherent equipment and processing design problems associated with multi-step processing in portable containers and without excessive losses of cell viability or physical losses of cells to adherence to equipment and container surfaces inside the container.

A number of feature refinements and additional features are applicable to the third aspect of the invention. These feature refinements and additional features may be used individually or in any combination. As such, each of the following features may be, but are not required to be, used with any other feature or combination of the third aspect or any other aspect of the disclosure.

In preferred implementations, the portable container may be a container of an apparatus of the first aspect or second aspect of the invention. A first side of the filter within the container may be a filtrate volume and a second side of the filter in the container may be a tissue retention volume of a container of an apparatus of the first aspect or second aspect. Alternatively, the portable container may be other than a container of the apparatus according to the first aspect or second aspect. The method may include, after centrifuging, removing the container from the centrifuge prior to the selectively removing.

The selectively removing may include inserting an aspiration tube from outside of to inside of the container to contact the pellet phase inside the container and aspirating at least a majority of material of the pellet phase through the aspiration tube to outside of the container without suspending material of the pellet phase in a suspension liquid. Aspirating the material of the pellet phase without first suspending the material in a suspension liquid is sometimes referred to herein as direct aspiration of the material of the pellet phase. Such direct aspiration may be performed without removal of lower-density material phases from above pellet phase, may be performed after removing some but not all of the lower-density material phases or may be performed after removing all of the lower-density material phases. The lower-density material phases may include an aqueous phase above the pellet phase and prior to the aspirating, the lower-density aqueous phase may be not removed from above the pellet phase. Such aqueous phase may be left substantially in-tact within the container during the aspirating, and may remain in the container following the aspirating. Some or all of the lower-density material phases may remain in the container after the aspirating. The inserting may comprise inserting the aspiration tube downward into the container from above. When lower-density material phases remain in the container during the aspirating, the aspiration tube may be inserted downwardly through the lower-density material phases and into the pellet phase material located below the lower-density material phases. The aspiration tube may be a needle (e.g., hypodermic needle), cannula or other device with a fluid communication channel. For many applications, a 18 to 22 gauge hypodermic needle may be used for the aspiration tube. During the aspirating, the aspiration tube may be in fluid communication with a fluid receptacle, and the aspirating may include collecting at least a majority of the material of the pellet phase in the fluid receptacle. Such a fluid receptacle may be a syringe or other fluid containment apparatus. By selectively removing the material of the pellet phase without requiring prior removal of less-dense material phases above the pellet phase, the process operation of removing the pellet phase material may be considerably simplified and the potential for processing errors and for loss of cells to adhesion to apparatus surfaces may be significantly reduced. The fluid receptacle may be pre-loaded with a dispersion medium that mixes with the material of the pellet phase in the fluid receptacle when the dispersion material is introduced into the fluid receptacle during the aspirating. The dispersion medium may be a liquid medium to disperse and suspend the cells of the pellet phase material. The dispersion medium may be a gel or gel-like material in which the cells of the pellet phase material may disperse and be retained. The dispersion medium may be a delivery vehicle for the cellular material (e.g., leuko stromal vascular cells) of the pellet phase, and such cellular material may be administered to a patient in a delivery composition including the cellular material and the dispersion medium. Some examples for a dispersion medium that may be pre-loaded into the fluid receptacle include compositions that may be or include one or more of the following, either alone or with other components: saline solution (e.g., a balanced saline solution, Hank's Balanced Solution), crystalloid solution (e.g., Lactated Ringer's solution), hyaluronic acid and hyaluronic acid-based materials. Such hyaluronic acid-based materials may be substrate or carrier compositions based on hyaluronic acid. Any of these listed materials for possible use as or inclusion in a dispersion medium may also be part of a final delivery composition for administration to a patient. The volume of dispersion medium pre-loaded into the fluid receptacle may be any convenient volume for the application. In some preferred implementations, the dispersion medium may be present in a sufficient volume to prevent clumping of material of the pellet phase in the fluid receptacle. The dispersion medium in the fluid receptacle may have a volume such that a volume ratio of the volume of the dispersion medium to the volume of the pellet phase material introduced into the fluid receptacle during the aspirating is at least 1:1, at least 2:1, or at least 3:1. Often, such a volume ratio may be up to 10:1, up to 7:1, up to 5:1; up to 3:1 or up to 2:1. In some implementations, the dispersion medium in the fluid receptacle may have a volume of at least 1 milliliter, at least 2 milliliters or at least 3 milliliters. In some implementations, the dispersion medium in the fluid receptacle may have a volume of up to 10 milliliters, up to 7 milliliters, up to 5 milliliters, up to 3 milliliters or up to 2 milliliters. A mixture formed in the fluid receptacle during the aspirating may be further processed to prepare a delivery composition including material of the pellet phase or the mixture may be in the form of a delivery composition that is ready as prepared in the fluid receptacle for direct administration to a patient, such as by direct injection from the fluid receptacle into the patient following completion of the aspirating. Further processing may include centrifuging the mixture formed in the fluid receptacle to reform a pellet phase, separation of the pellet phase material from other, typically less-dense material phases, that form during the centrifuging, followed by formulation of the pellet phase with other components to prepare a desired delivery composition, which could include any of the components that could be used as the dispersion medium or any other components suitable for a delivery composition. When the delivery composition is to be injected into a joint to treat osteoarthritis, the delivery composition may in some preferred implementations have a total volume in a range having a lower limit of 0.5 milliliter, 1 milliliter or 2 milliliters and an upper limit of 5 milliliters, 4 milliliters or 3 milliliters. The delivery composition may include a volume of the pellet phase material in a range having a lower limit of 0.25 milliliter, 0.5 milliliter, 0.75 milliliter, or 1 milliliter and an upper limit of 2.5 milliliters, 2 milliliters or 1.5 milliliters. When the pellet phase material includes a concentrate of leuko stromal vascular cells, the delivery composition will include a mixture of the different cells present in the leuko stromal vascular fraction, without purification and without culturing. This is distinguishable from other treatment compositions that may be prepared using only certain types of cells separated from the leuko stromal vascular fraction mixture or using cultured cells.

In some implementations, selective removal of material of the pellet phase may involve removing one or more, or all, of the lower-density material phases layers prior to removing material of the pellet phase from the container. When lower-density material phases are removed prior to removal of material of the pellet phase, removing the lower-density material phases may include removing such lower-density material phases from the container in sequence of increasing density, which may include suctioning the lower-density material phases from the container through open end of a suction conduit disposed in the container. Preferably, such an open end of a suction conduit may be disposed in the container not directly above the pellet phase, to reduce the possibility that suction created in the container would structurally disrupt the pellet phase. In some preferred implementations, the pellet phase remains in place and stationary, relative to the container, while the lower-density material phases are removed. In some implementations, removing the lower-density material phases may include tipping the container during suctioning of lower-density material phases to promote flow of at least a final suction portion of the lower-density material phases within the container laterally away from the pellet and toward the open end of the suction conduit. The container may include a corner located lateral to the pellet phase, and which may be located at an elevation of the container that is higher than the bottom elevation of the pellet phase, or even higher than a top elevation of the pellet phase. The tipping may promote flow of fluid of the lower-density material phases laterally toward the corner for suctioning from the vicinity of the corner into the open end of the suction conduit. In some preferred implementations, the lower-density material phases may be removed through a top of the container.

The method may include one or more steps other than or in addition to any or any combination of the steps noted above. Any such other or additional step may be performed between any of the steps noted above or may be performed prior to or after any of the steps noted above.

When lower-density material phases are removed from the container prior to removal of material of the pellet phase, the method may include, after the removing of the lower-density material phases, introducing aqueous suspension liquid into the container and dispersing cells of the pellet phase in the suspension liquid, such as to form a dispersion of the cells in the suspension liquid. The suspension liquid may be introduced at a volume in a range having a lower limit of 1, 2, 3 or 5 milliliters and an upper limit of 25, 20, 15 or 12 milliliters. A volume of suspension liquid of about 10 milliliters may be used for many implementations. A volume ratio of the suspension liquid to the volume of the pellet phase may be in a range having a lower limit of 1:1, 2:1, 3:1 or 5:1 and an upper limit of 25:1, 20:1, 15:1 or 12:1. A volume ratio of about 10:1 may be used in many implementations. After being dispersed in a suspension liquid, the suspension liquid with dispersed cells may be removed from the container. Preferably at least most of the suspension liquid is removed from the container and more preferably substantially all of the suspension liquid and substantially all of the cells from the pellet phase are removed from the container with the suspension liquid. The suspension liquid and dispersed cells may be removed through a top of the container, even though suspension liquid and dispersed cells may be removed from a location adjacent a bottom of the container. This suspension liquid and dispersed cells may be removed upward through a hollow member disposed downward into the container, for example through a hollow needle or cannula. In some implementations, such a hollow member may pierce and extend across the filter. Such a hollow member may be an aspiration tube, as described above, and may be in fluid communication with a fluid receptacle, as described above.

After the selectively removing, the pellet phase material removed from the container may be further processed and/or mixed with other components as desired, for example to prepare a desired delivery composition for administration to a patient. When the pellet phase material is first suspended in suspension liquid in the container before removal, the further processing may include centrifuging the mixture, recovering the pellet phase material and formulating the pellet phase material to prepare a delivery composition. Such a delivery composition may be or have features as described above.

For the digesting, digestion medium may be added to the container at a volume ratio of the volume of digest medium to volume of adipose tissue within the container is in a range of from 0.6:1 to 2:1 and wherein the digestion medium provides from 150 to 300 collagen digestion units (CDU) per milliliter of catalytic volume, and wherein the catalytic volume is the total of the volume of digestion medium and the volume of adipose tissue within the container. The digesting may comprise, after adding the volume of digestion medium, permitting enzymatic digestion within the container for a retention time in a range of from 20 minutes to 50 minutes while the container is disposed in a temperature controlled environment with the temperature controlled environment maintained within a temperature range of from 32° C. to 38° C. and with at least occasional agitation of contents within the container.

The digestion medium may provide collagen digestion units (CDU) per milliliter of catalytic volume within a range that is narrower than the range listed above. Such a range may have a bottom limit of 150, 175 or 200 CDU and an upper limit of 300, 275 or 250 CDU. In some implementations, the digestion medium may provide about 225 CDU per millimeter of catalytic volume. In this regard, the catalytic volume is the total volume of the digestion medium added to the container and the volume of adipose tissue already disposed within the container when the digestion medium was added. For example, if the volume of digestion medium added to the container equals the volume of adipose tissue already disposed within the container, then the digestion medium will need to contain a concentration of collagenase enzyme that is twice as large as the desired concentration relative to the catalytic volume. As will be appreciated, the adipose tissue as collected will have associated contaminants, but in preferred applications with thorough washing, the adipose tissue should be cleaned of most contaminants so that substantially all of the volume of material on a tissue retention side of the filter in the container may be adipose tissue.

The volume ratio of digestion medium to adipose tissue may be in a narrower range than that described above. Such a volume ratio may have a lower limit of 0.6:1, 0.75:1 or 0.9:1 and may have an upper limit of 2:1, 1.75:1, 1.5:1 or 1.25:1. For various implementations, the volume ratio of digestion medium to washed adipose tissue may be about 1:1.

The retention time during the digesting may be within a narrower range than that described above. The retention time may be in a range having a lower limit of 20 minutes, 25 minutes or 30 minutes and an upper limit of 50 minutes, 45 minutes or 40 minutes. For various implementations, the retention time may be about 35 minutes.

The digesting may include continuous agitation of the contents during some portion or substantially all of the retention time. The agitation may include mixing, periodically or continuously, with a rotatable mixer disposed within the container. The agitation may include periodic or continuous movement of the container to cause agitation of contents within the container. The agitation may include shaking the container, such as on a warmer-shaker. A temperature controlled environment may be provided by a warmer-shaker.

Temperature control may be implemented at various points in the processing of the method. Digestion medium when added to the container may be within a temperature range having a lower limit 32° C., 33° C., 34° C. or 35° C. and an upper limit of 38° C. or 37° C. The temperature within a temperature controlled environment during digestion may be maintained in a narrower range than that stated above. A temperature controlled environment may be maintained within a temperature range having a lower limit of 32° C., 33° C., 34° C. or 35° C. and an upper limit of 38° C. or 37° C. Wash liquid, when added to the container, may be within a temperature range having a lower limit of 32° C., 33° C., 34° C. or 35° C. and an upper limit of 38° C. or 37° C.

The washing may include at least one wash cycle or multiple wash cycles, with each wash cycle comprising: adding a volume of aqueous wash liquid to the container to contact the adipose tissue within the container; mixing the wash liquid and the adipose tissue in the container; and removing at least a majority of the wash liquid with contaminants from the container on a first side (e.g., filtrate volume) of the filter and retaining at least most of the adipose tissue in the container disposed on a second side of the filter (e.g., tissue retention volume). For each wash cycle, a volume ratio of wash liquid addition may be controlled. The volume ratio of wash liquid addition refers to a volume ratio of the volume of wash liquid to a volume of adipose tissue within the container to which the wash liquid is being added during the wash cycle. The volume ratio of wash liquid addition may be in a range having a lower limit of 0.5:1, 0.7:1 or 0.8:1 and an upper limit of 4:1, 3:1, 2:1 or 1.5:1. For many implementations, the volume ratio of wash liquid addition may be about 1:1. A cumulative volume ratio of wash liquid addition may be at least 2:1, or at least 3:1. The cumulative volume ratio of wash liquid addition refers to a sum of the volume ratios for all of the wash cycles.

The washing may include more than two wash cycles. In some implementations, the washing may comprise at least three wash cycles. For many implementations, three wash cycles may be sufficient, while for other implementations, two wash cycles may be sufficient.

Each wash cycle may comprise removing wash liquid (preferably at least a majority of the wash liquid and more preferably substantially all of the wash liquid) by suctioning from the filtrate volume of the container on the first side of the filter. During such suctioning, the wash liquid may be removed through a top of the container.

Mixing the wash liquid may include operating a rotatable mixer disposed in the container. The rotatable mixer may be manually operable, such as by a handle attached to a rotating shaft disposed through a top of the container. The mixing may include manually (hand) manipulating such a handle to manually rotate the mixer within the container. In various preferred implementations, such mixing may be performed following addition of the wash liquid, and preferably shortly following such addition, to thoroughly mix the wash liquid and the adipose tissue being washed. Such a rotatable mixer may also be used to mix the digestion medium and the adipose tissue following addition of the digestion medium to the container, and preferably shortly after such addition, to thoroughly mix the digestion medium and washed adipose tissue to be digested.

The wash liquid used during the washing may but need not be of the same composition for each wash cycle. The wash liquid may include one or more additives. For example the wash liquid for one of more of the wash cycles may include one or more than one of an anti-clotting agent, an antibiotic and an antifungal. In some preferred implementations, for at least one wash cycle, the wash liquid includes at least one of an anti-clotting agent, an antibiotic or an antifungal. In other implementation, for at least one wash cycle, the wash liquid includes an anti-clotting agent, an antibiotic and an antifungal. One preferred example for an anti-clotting agent is heparin.

The method may include, not later than 50 minutes following adding of the volume of digestion medium, adding a stopping reagent to the container to stop enzymatic activity within the container. The adding of a stopping reagent to the container may be performed within a narrower time period than that described above. The digestion medium may be added within a time period not later than 45 minutes following adding the volume of digestion medium, not more than 40 minutes following adding the volume of digestion medium or not more than 35 minutes following adding of the volume of digestion medium. The stopping reagent may comprise human albumin. The stopping medium may be added in an amount sufficient to substantially stop enzymatic activity within the container. The stopping reagent may preferably be added before the centrifuging of the container following the digesting.

The container may be conveniently transported between different locations for performance of different processing at the different locations, and preferably may be manually transported by being carried by a person. For example, a temperature controlled environment may be located at one location and the centrifuge may be located at a different location, and the method may comprise after the retention time in a temperature controlled environment, transporting the container from that location to the location of the centrifuge for performance of the centrifuging. As another example, one or more wash cycles may occur at yet a different location, and the method may comprise transporting the container from the location of a wash cycle to the location of a temperature controlled environment. By transporting the container from one location to another it is meant that the container, along with contents of the container, are physically moved from one location to the other location, whether or not there are intermediate stops along the way.

The method permits convenient and controlled processing of significant quantities of adipose tissue in a convenient manner. The volume of adipose tissue (including contaminants), disposed in the tissue retention volume of the container on the second side of the filter at commencement of the washing may be in a range having a lower limit of 50, 100, 150, 200 or 250 cubic centimeters and an upper limit of 700, 600, 500, 400, 300 or 200 cubic centimeters, provided that the upper limit is larger than the lower limit.

It should be appreciated that when reference is made to "adipose tissue" or a volume thereof in relation to a method of the invention the reference may be to in-tact adipose tissue and any associated contaminants that are present with the in-tact tissue. These contaminants come from the biological materials extracted from subjects to obtain the adipose tissue. Contaminants that may be associated with the adipose tissue include for example blood, free lipids, small particles and debris and other materials that may have been collected with the adipose tissue or result from degradation during tissue collection or processing operations. The amounts of these contaminants will generally be higher in unwashed adipose tissue at the commencement of washing operations and will generally be lower at the commencement of digesting operations, following the washing.

A fourth aspect of the disclosure is provided by a method of processing adipose tissue using an apparatus of the first aspect or the second aspect. The method includes processing in the container of the apparatus, including washing adipose tissue within the container to remove contaminants from the adipose tissue. The washed adipose tissue may be used, for example, for preparing a fat graft.

A number of feature refinements and additional features are applicable to the fourth aspect of the invention. These feature refinements and additional features may be used individually or in any combination. As such, each of the following features may be, but are not required to be, used with any other feature or combination of the fourth aspect or any other aspect of the disclosure.

The washing may include any feature or combination of any features discussed in relation to the third aspect of the invention. After the washing, washed adipose tissue may then be removed from the apparatus, before or after mixing additives into the washed adipose tissue, for example for use in a fat graft.

A fifth aspect of the disclosure is provided by uses of concentrate of leuko stromal vascular cells from adipose tissue for treatment of osteoarthritis.

A treatment composition for use to treat osteoarthritis may comprise a concentrate of a mixture of leuko stromal vascular cells as recovered from processing of adipose tissue, for example without purification of a specific cell type or cell types from the stromal vascular fraction mixture and without culturing cells. The composition may be or include any delivery composition or feature thereof described in relation to the third aspect or any other aspect of the disclosure.

A method for treating osteoarthritis may include administration to a patient of such a treatment composition. The administration may involve injection of the treatment composition into or in the vicinity of a joint to be treated for osteoarthritis. The administration may be by injection from a fluid receptacle (e.g., syringe) into which pellet phase material is directly aspirated and in which the treatment composition was prepared to include dispersion medium pre-loaded into the fluid receptacle, for example as described above.

A sixth aspect of the disclosure is provided by a method for recovering a concentrate product comprising leuko stromal vascular cells from adipose tissue. The method includes directly aspirating from a processing container pellet phase material prepared from processing adipose tissue in the container. The pellet phase material may be or have any feature or combination of any features of described with respect to any other aspect of the disclosure. The pellet phase material may have been formed in the container by any method described with respect to any other aspect of the disclosure. The container may be an apparatus as described with respect to any other aspect of the disclosure. These and other aspects of the invention will be further understood by reference to the drawings and the exemplary description provided below.

DETAILED DESCRIPTION OF PREFERRED EMBODIMENTS

The following description of embodiments may be exemplified by reference to collecting and processing tissue comprising adipose, but the principles described apply also to collection and processing of other tissue.

Figure 1:
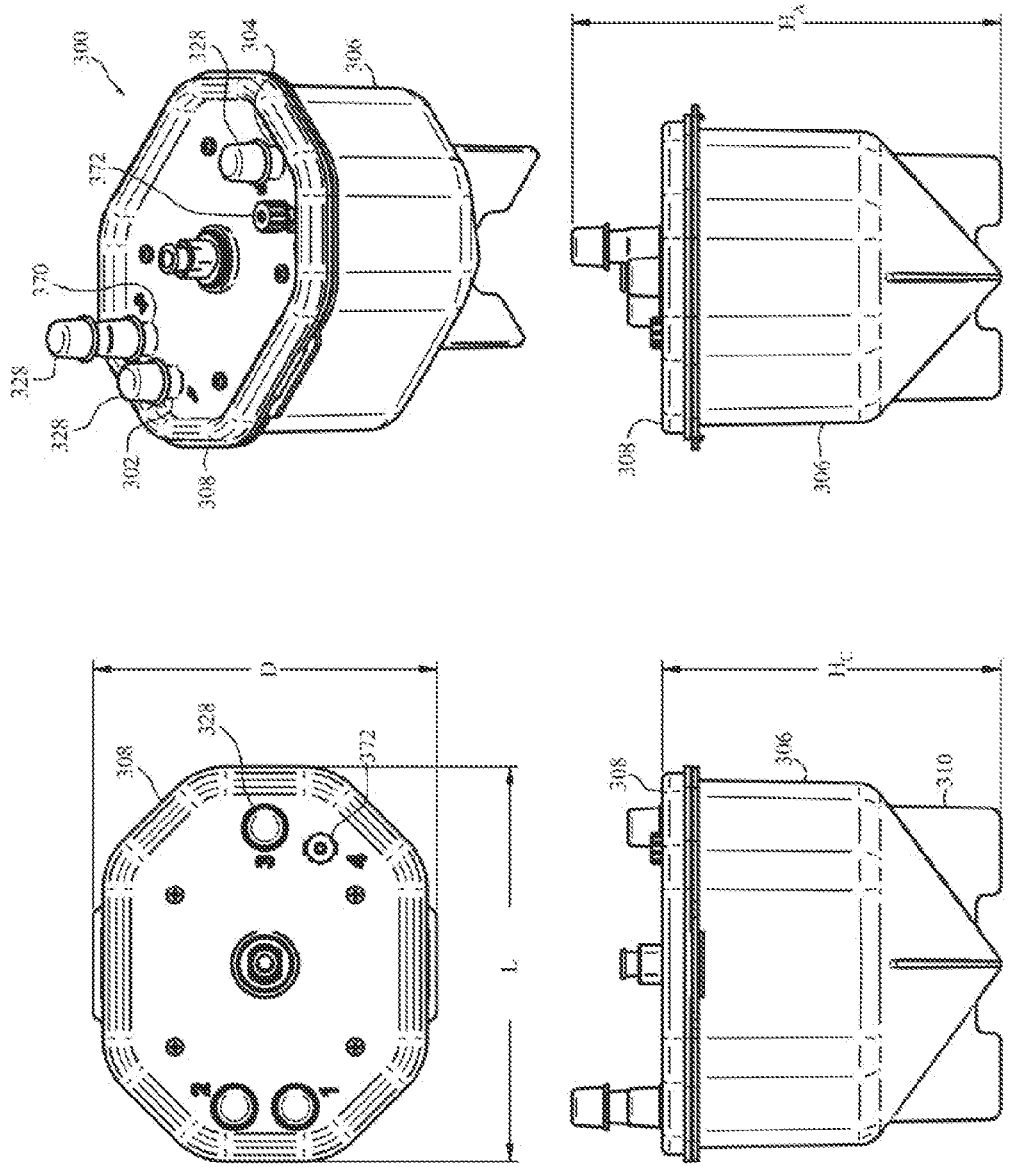
FIG. 1 shows top, perspective, side and end views of an embodiment of a tissue collection and processing apparatus.

Reference is made to FIGS. 1-11 concerning features of an apparatus 300 useful for collection of tissue comprising adipose removed from a patient during a lipoplasty procedure and/or for post-collection, multi-step processing of collected adipose in a single container. In FIG. 1, the apparatus 300 is illustrated in a collection orientation. The collection orientation is the orientation in which the apparatus 300 may be placed during the collection of adipose removed from a patient during a lipoplasty procedure. The apparatus 300 may also be placed in the collection orientation during stages of the post-collection processing of collected tissue as described below. Accordingly, subsequent references herein to the orientation of the apparatus 300, such as top, bottom, lower and upper, will refer to such a collection orientation. As illustrated, the apparatus 300 has an apparatus height $H_A$, an apparatus length L, and an apparatus depth (or width) D. The apparatus 300 also includes a suction port 302 and an inlet port 304. The suction port 302 and inlet port 304 are disposed on the top of the apparatus 300 when the apparatus 300 is in the collection orientation as illustrated in FIG. 1. In FIG. 1, and in certain other subsequent figures, the ports are illustrated as having caps 328 thereon. Such caps 328 are used to cover the various ports and may be removed and replaced as necessary during use of the apparatus 300.

The apparatus 300 includes a shell 306 and a lid 308. The shell 306 is a unitary bowl-like member where the only access into the interior, or cavity of the shell 306 is through the opening at the top of the shell 306. As illustrated in FIG. 1, this opening at the top of the shell 306 may be covered by the lid 308. The lid 308 and shell 306 may be rigid. The lid 308 and shell 306 are each preferably made of a clear polymeric material, such as a clarified polypropylene polymer composition, which provides low cellular adhesion and reasonable clarity. The lid 308 and shell 306 may be fabricated by injection molding. The lid 308 may be attached to the shell 306 in any appropriate manner, including snapping, clamping and/ or gluing onto the shell 306. Together, the shell 306 and lid 308 form a container 322 with an internal containment volume 330 (see FIG. 5 and accompanying discussion below) within the apparatus 300. The internal containment volume 330 is the volume within the cavity of the shell 306 covered by the lid 308, and is the volume available for disposing both hardware and material tissue to be processed in the container. This container may have a container height $H_C$. The shell 306 may include a set of integral base supports 310 that may support the apparatus 300 in the collection orientation when the apparatus is placed on a horizontal surface. The apparatus height $H_A$ is larger than the container height $H_C$ by the distance of projections above the top of the container for the inlet port 304, suction port 302, caps 328 and other upward projecting features described below. The shell 306 may be conveniently designed to efficiently fit within a centrifuge bucket. The projections above the container height $H_C$ may be configured so as not to interfere with operation of such a centrifuge. As seen in FIG. 1, the apparatus length L is equal to the container length and the apparatus depth is equal to the container depth (or width). As will be appreciated, the corresponding height, length and depth dimensions of the internal containment volume 330 will equal the height, length and depth dimensions of the container less the corresponding thicknesses of walls of the shell 306 and lid 308. As shown in FIG. 1, some features may be integrally formed with the lid 308. For example as shown in FIG. 1 the suction port 302 and the inlet port 304 are integrally formed as a unitary fabricated piece with the lid 308. It should be appreciated that such features may be provided as separate pieces and then assembled, such as by gluing or other means. For structural integrity, fabrication as a unitary piece is generally preferred.

Figure 2:
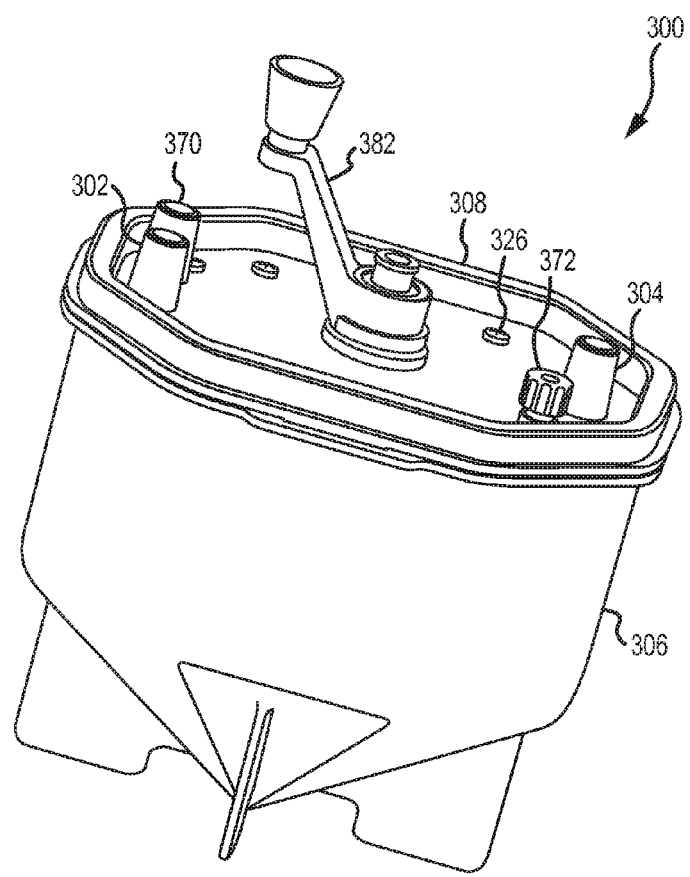
FIG. 2 shows another perspective view of the same tissue collection and processing apparatus as FIG. 1.
Figure 3:
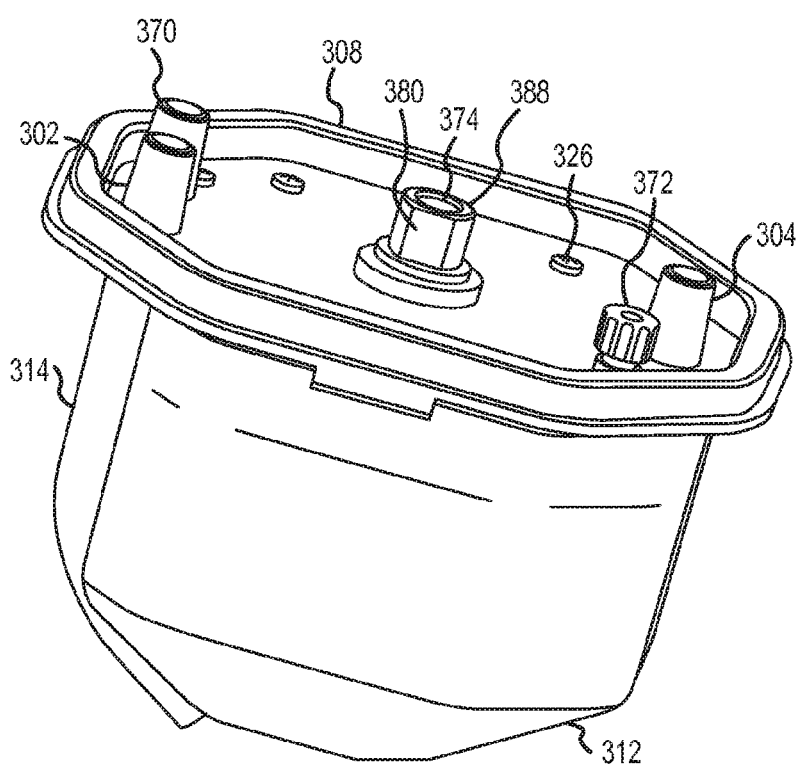
FIG. 3 shows the same tissue collection and processing apparatus as FIG. 2 with a shell removed.

FIG. 2 shows another perspective view of the apparatus 300 with the caps 328 to ports removed and with an installed handle 382. FIG. 3 shows the apparatus 300 in the same orientation as in FIG. 2 with the shell 306 and handle 382 removed. With the shell 306 removed, a filter 312 can be seen that is disposed within the internal containment volume 330. The filter 312 may have a separation size in a range appropriate for the internal application (e.g., fat graft or preparation of cell concentrate). The filter is preferably made of a mesh material. One preferred mesh material is a nylon mesh. Also visible within the internal containment volume 330 is a suction port conduit 314 extending downward from the suction port 302. Additionally, as illustrated in FIG. 3, all components of the apparatus 300, except for the shell 306, are interconnected to the lid 308. In this regard, the subassembly shown in FIG. 3 may be assembled as shown and inserted into the shell 306.

Figure 4:
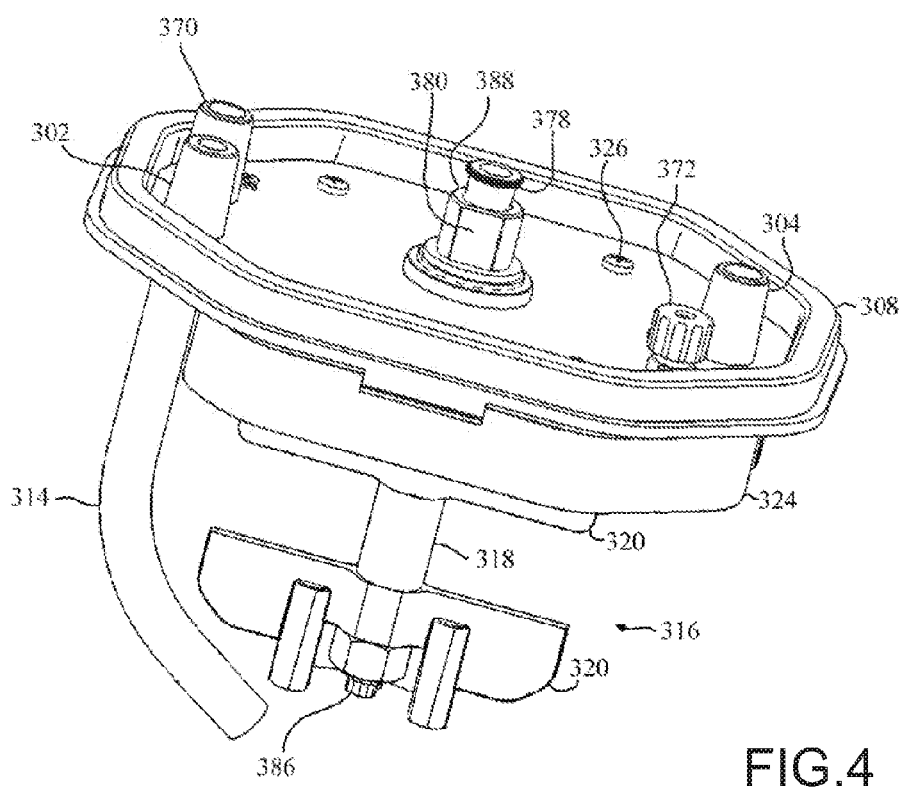
FIG. 4 shows the same tissue collection and processing apparatus as FIG. 3 with a filter removed.

FIG. 4 shows another perspective view of the apparatus 300. FIG. 4 shows the apparatus 300 in the same orientation as in FIG. 3 with both the shell 306 and the filter 312 removed. With the filter 312 removed, a flow barrier skirt 324 extending downward from the lid 308 into the internal containment volume 330 is visible. In an example, the flow barrier skirt 324 may extend between 5 mm and 50 mm downward from the lid 308. The flow barrier skirt 324 may serve as an attachment point for the filter 308 such that the filter 312 may be fixed relative to the lid 308. The flow barrier skirt 324 may also serve to prevent material from entering a tissue retention volume 332 (described below) and immediately moving through the filter 312 into the filtrate volume 334. The tissue retention volume 332 is that portion of the internal containment volume 330 contained within the filter 312 and barrier skirt 324 below the lid 308. The filtrate volume 334 is that portion of the internal containment volume 330 disposed outside of the filter 312 and barrier skirt 324. With the flow barrier skirt 324 in place, and material entering the inlet port 304 must at least move to below the lowest level of the flow barrier skirt 324 before it is able to pass through the filter 312 into the filtrate volume 334. The flow barrier skirt 324 may be part of a filter subassembly that includes the flow barrier skirt 324 and the filter 312. This subassembly is mounted to the lid 308 with four screws 326.

The filter 312 is asymmetric with respect to the lid 308 and shell 306 in that it is configured to provide clearance between its left side (as viewed in FIG. 3) and the shell 306 for the suction port 302 and suction port conduit 314. A portion of the filter 312 may be disposed about (e.g., rest on or around) a portion of the suction port conduit 314.

With the filter 312 removed (FIG. 4), a mixing device 316 can be seen. The mixing device 316 includes a rotatable shaft 318 and a set of mixing members 320. The axis of rotation of the rotatable shaft 318 may be through a central axis of the rotatable shaft 318. The mixing members 320 are in the form of paddles extending outward from the rotatable shaft 318. Accordingly, when the rotatable shaft 318 is rotated, the mixing members 320 will be rotated through the materials within the tissue retention volume 332 to aid in mixing the materials within the internal containment volume 330, and in particular within the tissue retention volume 332. The rotatable shaft 318 extends from outside of the internal containment volume 330 through the lid 308 to the inside of the internal containment volume 330. As the rotatable shaft 318 is rotatable relative to the lid 308, the mixing members 320 fixed to the rotatable shaft 318 are also rotatable relative to the lid 308. The rotatable shaft 318 may be made from a metal composition, such as stainless steel (e.g., grade 303, 304, or 316). Alternatively, the rotatable shaft 318 may be made from a high-strength polymer composition such as an Ultem™ resin product.

The rotatable shaft 318 may include a handle interface 380 (FIG. 3) that may provide an interface for the handle 382 (FIG. 2) to be interconnected to the portion of the rotatable shaft 318 outside of the internal containment volume 330. The handle interface 380 of FIG. 3 is in the form of a pair of parallel surfaces disposed about the portion of the rotatable shaft 318 outside of the internal containment volume 330. The handle 382 has a mating pair of interior parallel surfaces configured such that when the handle 382 is placed over the handle interface 380, turning the handle 382 will result in turning the rotatable shaft 318 and the mixing device 316. Such an interface 380 also allows for the handle 382 to be removed from and replaced on the handle interface 380 as needed during use of the apparatus 300.

Figure 5:
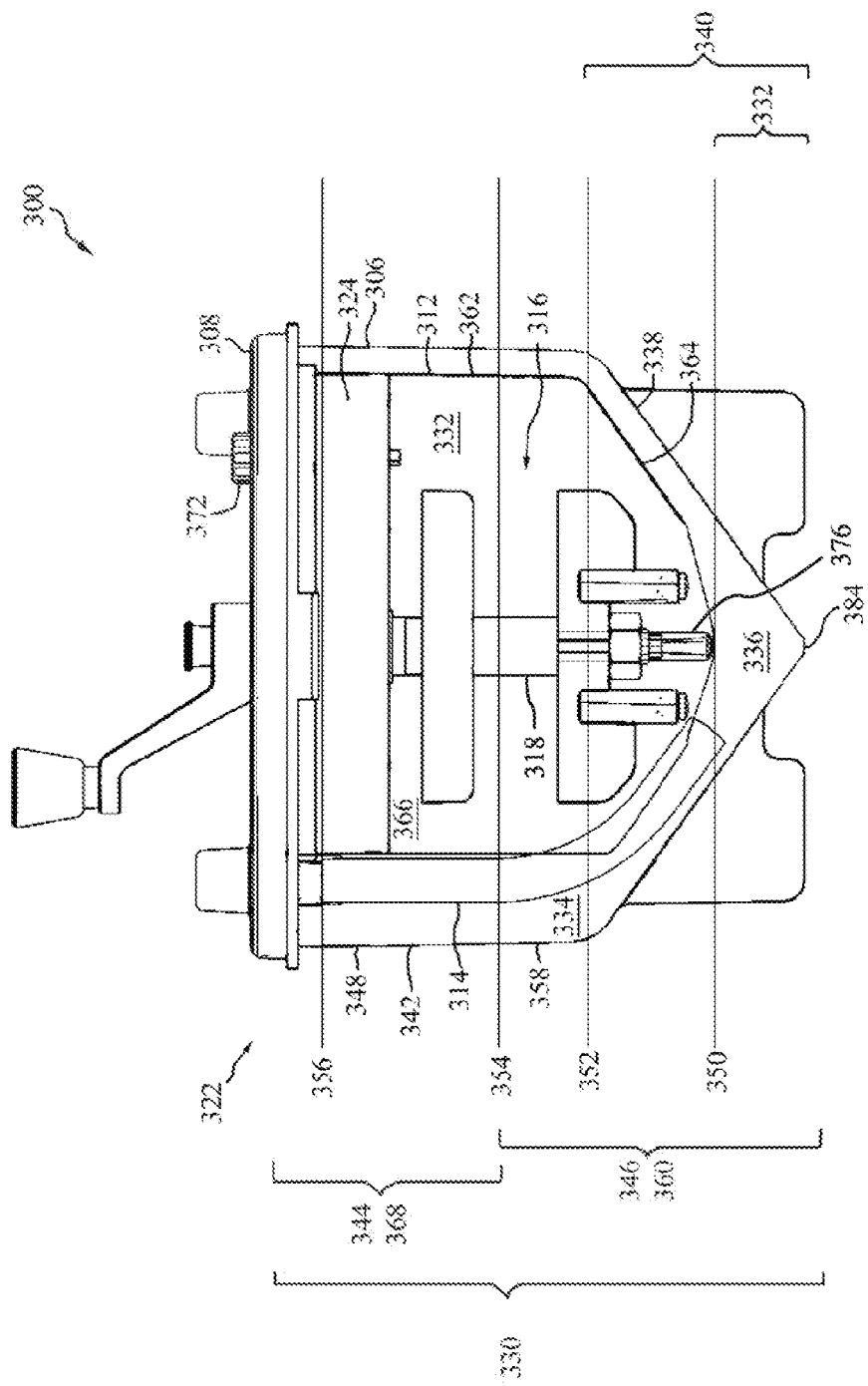
FIG. 5 illustrates various regions within the tissue collection and processing apparatus of FIG. 2.

FIG. 5 is a side schematic view of the apparatus 300 showing the mixing device 316 and filter 312 within the shell 306. The internal containment volume 330 is the entire volume within the shell 306 and under the lid 308. Together, the portions of the shell 306 and lid 308 that contain the internal containment volume 330 are a container 322 of the apparatus 300. The filter 312 divides and separates the internal containment volume 330 of the container 322 into the tissue retention volume 332 disposed inside the filter 312, and a filtrate volume 334 disposed within the shell 306 on the outside of the filter 312. The filtrate volume 334 is that portion of the internal containment volume 330 into which filtrate enters after passing through the filter 312 from the tissue retention volume 332.

Disposed within the internal containment volume 330 at the bottom of the shell 306, below a level 350 that is at or below the lowest extent of the filter 312 (and therefore also below the lowest extent of the tissue retention volume 332), is a collection volume 336, such that the collection volume 336 occupies the lowermost portion of the filtrate volume 334 located below the lowest elevation of the tissue retention volume 332.

The shell 306 has a tapered wall portion 338 that defines a tapered portion 340 of the internal containment volume 330, such that the cross-sectional area of the tapered portion 340 of the internal containment volume 330 tapers with a reducing cross-sectional area in a direction toward bottom of the container 322. By tapering, it means that the cross-sectional area in a horizontal plane (assuming the apparatus 300 is in the collection orientation) becomes smaller in the direction of the taper (e.g., a direction orthogonal to the horizontal plane). The tapered portion 340 of the internal containment volume 330 occupies the portion of the internal containment volume 330 below a level 352 where the tapered wall portion 338 meets a straight wall portion 342 of the shell 306. The tapered wall portion 338 is shown as having a flat, uniform inclined wall surface. The incline angle of surfaces of the tapered wall portion need not be uniform from the top to the bottom of the tapered portion 340 of the internal containment volume 330, and may vary from top to bottom with portions with different incline angles, and may have a curved surface, provided that the cross-sectional area is reducing in the direction of the taper. Also, the tapered wall portion 338 need not be uniform around the perimeter of the tapered portion 340 of the internal containment volume 330. For example, in the embodiment in FIGS. 3-5, the tapered wall portion 338 has a steeper incline on the ends than on the front or back of the apparatus 300.

The shell 306 may comprise an upper portion 344 generally above a level 354 and having a first wall surface portion 348 defining a corresponding upper portion 368 of the internal containment volume 330. Substantially all of the first wall surface portion 348 may have an incline relative to horizontal of at least 75°. For example, substantially all of the first wall surface portion 348 may be substantially vertical (90° incline relative to horizontal). The shell 306 may include a lower portion 346 located below the upper portion 344 and having a second wall surface portion 358 defining a corresponding lower portion 360 of the internal containment volume 330. The lower portion 360 may include the tapered wall portion 338 defining the tapered portion 340 of the internal containment volume 330. Substantially all of the tapered wall portion 338 may preferably have an incline relative to horizontal in a range of from 30° to 60°, although other angles or curved surfaces may be used. The tapered portion 340 of the internal containment volume 330 may occupy substantially the entire lower portion 360 of the internal containment volume 330. At least a first portion 362 of the filter 312 may be disposed in the upper portion 368 of the internal containment volume 330 and a second portion 364 of the filter 312 may be disposed in the lower portion 360 of the internal containment volume 330. The tapered wall portion 338 may form a nadir 384 at its lowest elevation. The nadir 384 may also be a nadir of the collection volume 336, the filtrate volume 334, the container 322, and the internal containment volume 330.

The internal containment volume 330 may include an available processing volume or "useable" volume 366 which may be the portion of the internal containment volume 330 that is usable and/or may normally be occupied by materials within the container 322 during normal use. For example, the available processing volume 366 may be the portion of the internal containment volume 330 below a level 356 that coincides with the bottom extension of a port through the lid 308 and that is not occupied by portions (e.g., internal hardware) of the apparatus 300 within the internal containment volume 330, such as the mixing device 316, barrier skirt 324, filter 312 and suction port conduit 314. The top of the available processing volume may be at the elevation of the bottom extension of the inlet port 304, which may define a maximum fill level within the internal containment volume 330.

The inlet port 304 in fluid communication with the tissue retention volume 332 through the lid 308 is configured for introducing tissue comprising adipose directly into the tissue retention volume 332 during a lipoplasty procedure. However, use of the apparatus 300 is not so limited, and the tissue may be introduced into the apparatus using tissue previously collected in another container and transferred to the apparatus 300. An additional access port 372 in fluid communication through the lid 308 with the tissue retention volume 332 provides an additional route into the tissue retention volume 332, for example for introduction of additives.

The suction port 302 is in fluid communication through the lid 308 with the filtrate volume 334 via suction port conduit 314 extending from the suction port 302 to within the tapered portion 340 of the internal containment volume 330 in the vicinity of the top of the collection volume 336. The suction port 302 is configured for connection to a vacuum system, for example through connection of a suction conduit through which suction may be applied by a vacuum system to suction from the filtrate volume 334 material passing through the filter 312 from the tissue retention volume 332 into the filtrate volume 334.

The rotatable shaft 318 may include a filter contact member 376 (FIG. 5) that is offset from an axis of rotation of the rotatable shaft 318. A lower end of the filter contact member 376 may contact a portion of the filter 312 as illustrated in FIG. 5. As the rotatable shaft 318 is rotated, the filter contact member 376 may rotate in a circular path about the axis of rotation of the rotatable shaft 318 remaining in contact with and moving along a portion of the filter 312. This contact may cause the filter 312 to deform and such deformation and/or the contact between the filter contact member 376 and filter 312 may cause materials that may have adhered to the filter 312 in this region to become dislodged from the filter 312. Thus, the filter contact member 376 may assist in keeping the filter 312 from clogging and increasing the effectiveness of the filter 312.

The rotatable shaft 318 may include a lumen 374 therethrough. The top of the lumen 374 is visible in FIG. 3. The lumen 374 may have a distal end 386 (FIG. 4) within the tissue retention volume 332 and a proximal end 388 (FIG. 3) outside of the internal containment volume 330 and thus may allow access to the tissue retention volume 332 therethrough. The lumen 374 may be disposed along the central axis of the rotatable shaft 318. The lumen 374 thus provides a conduit for accessing the internal containment volume 330. As further described below, the lumen 374 may provide access for removing processed material from the internal containment volume 330. In that respect, the opening through the lid 308 through which the rotatable shaft 318 extends acts as an extraction port through which access is provided via the lumen 374 that passes through such opening. The apparatus 300 may include a plug 378 (shown in FIG. 4 and not shown in FIG. 3) that may be placed in the proximal end 388 of lumen 374 to seal the lumen 374.

Figure 6:
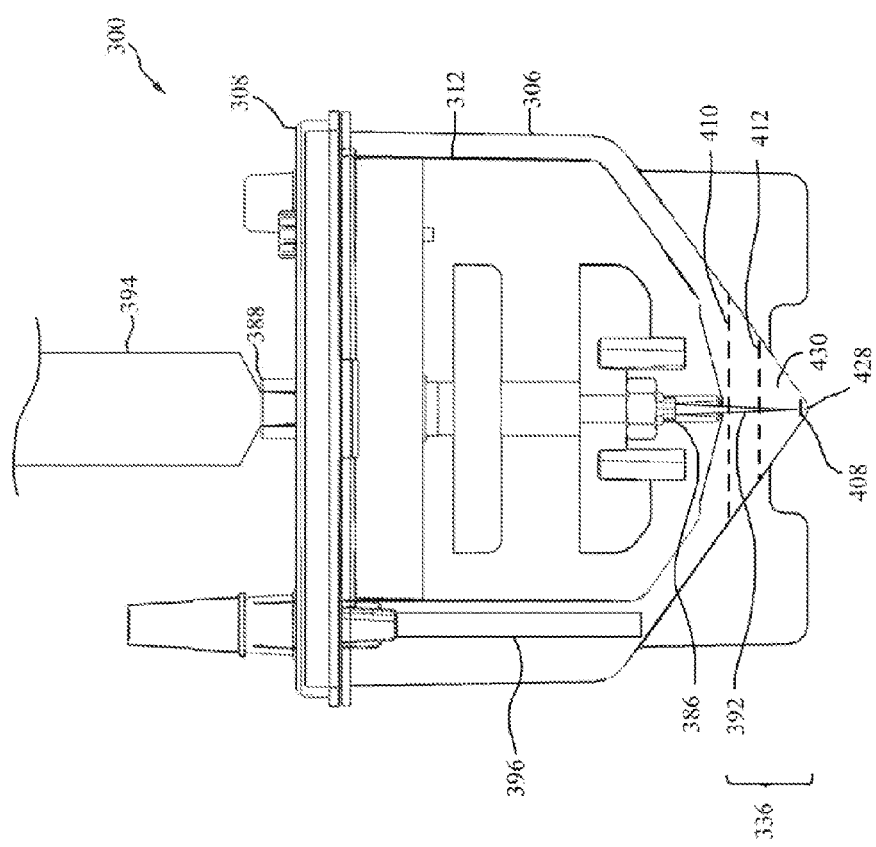
FIG. 6 illustrates a needle inserted into a tissue collection and processing apparatus.
Figure 7:
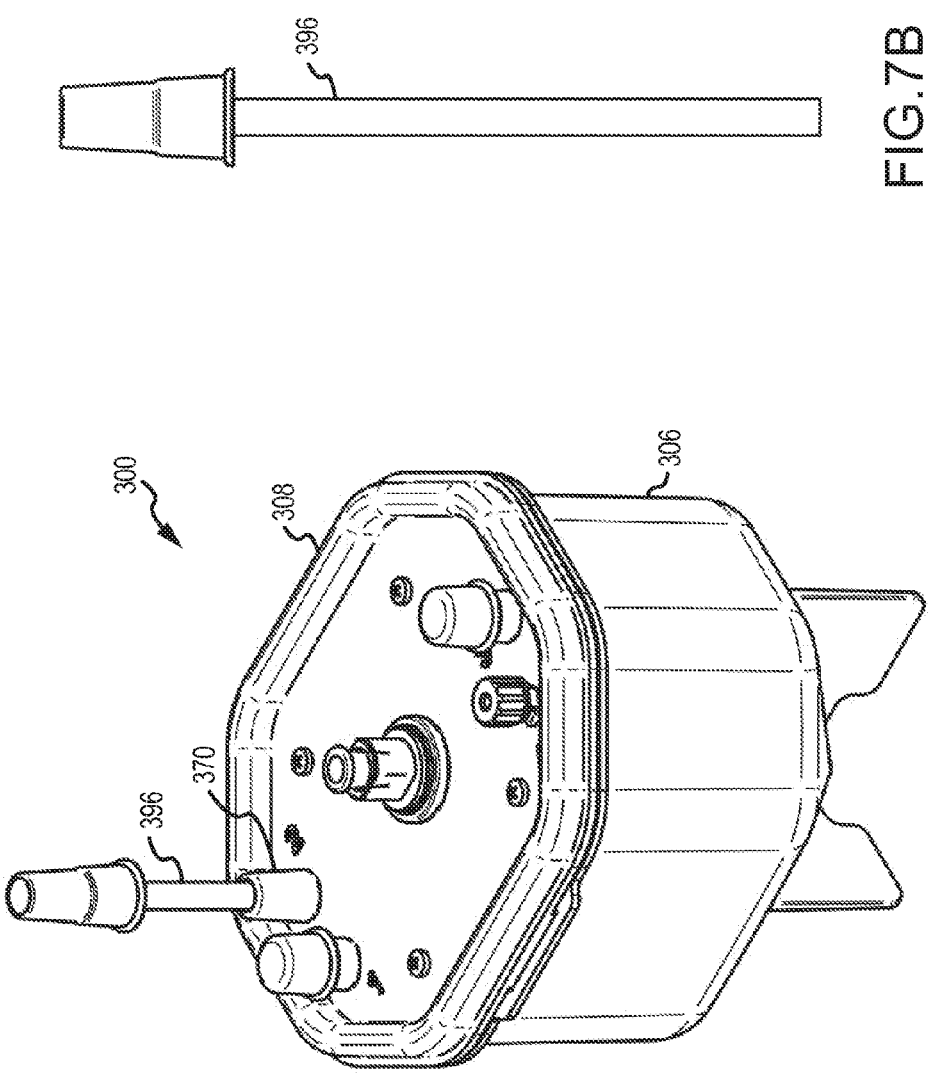
FIGS. 7A and 7B illustrate a translatable conduit in a tissue collection and processing apparatus.

As shown in FIG. 6, a hypodermic needle 392 may be inserted through the lumen 374 and may be advanced out of the distal end 386 of the lumen 374 and to pierce through the filter 312 to directly access the collection volume 336 (the volume under the line 410 in FIG. 6). Thus, the hypodermic needle 392 may be used to inject material into, or remove (aspirate) material from the collection volume 336. Additionally, as the axis of the lumen 374 is vertically oriented, access to the collection volume 336 using the hypodermic needle 392 is by downward vertical insertion into the lumen 374 from above the container. Such vertical insertion coupled with the ability of the apparatus 300 to be placed on a flat surface in the collection orientation, allows for user-friendly access to the collection volume 336, and helps avoid complications that could compromise operations to collect valuable processed material from the collection volume 336.

The hypodermic needle 392 may be interconnected to a syringe 394. The proximal end 388 of the lumen 374 may include a tapered receptacle adapted to mate with a tapered tip of the syringe 394. In this regard, as shown in FIG. 6, the depth of penetration by the hypodermic needle 392 into the collection volume 336 when the tapered tip of the syringe 394 is in contact with the tapered receptacle of the lumen 374 may be controlled by controlling the length of the hypodermic needle 392 extending from the syringe 394. Additionally, the proximal end 388 of the lumen 374 may include a feature, such as a notch, to retain an o-ring (not shown) such that when the syringe 394 is positioned against the proximal end 388 of the lumen 374, the o-ring forms a seal between the proximal end 388 of the lumen 374 and the syringe 394 (i.e., a seal through the o-ring between a wall surface in the tapered receptacle and an exterior wall surface of the tip of the syringe inserted into the tapered receptacle).

Turning to FIGS. 7A and 7B, the second suction port 370 includes a translatable member 396 that may be translated up and down relative to the lid 308 to vary the depth (elevation within the filtrate volume 334) at which material from the filtrate volume 334 is drawn through the second suction port 370. Examples of the various depths (elevations) at which the translatable member 396 may be positioned are illustrated in FIGS. 7A, 8, 9, and 11 and are discussed below in relation to methods of using the apparatus 300. The fit between the translatable member 396 and the opening through the lid 308 of the second suction port 370 is such that the translatable member 396 may be readily translated up and down to a desired level, while maintaining a tight enough fit to allow a vacuum applied to the translatable member 396 to adequately draw material out of the filtrate volume 334.

In general, the parts discussed with reference to the apparatus 300 may be made from any appropriate biocompatible material. In particular, the shell 306 may be made from a biocompatible transparent polymer material to allow inspection of the contents therein. Screws 326 and the rotatable shaft 318 may be made from metal, such as stainless steel. Other parts of the assembly 300 pictured in FIG. 1 may be made from appropriate biocompatible polymers.

Various exemplary dimensions of one specific nonlimiting example of an apparatus 300 will now be described with reference to FIGS. 1 and 5. In this example, the apparatus 300 has apparatus height $H_A$ of about 157 mm, an apparatus length L of about 145 millimeters, and an apparatus depth D of about 126 millimeters. The containment volume height $H_C$ is about 124 millimeters. The example has an available processing volume 366 of about 760 milliliters and a collection volume 336 of about 23 milliliters. The portion of the tissue retention volume 332 that coincides with the available processing volume 366 is about 580 milliliters. As will be appreciated, a milliliter is equal in volume to a cubic centimeter, and the volumes listed here in milliliters may be equivalently stated as cubic centimeters.

In a method for processing tissue from a lipoplasty procedure using the apparatus 300, the tissue may be subjected to multi-step processing within the internal containment volume 330 to prepare within the apparatus 300 a concentrated product comprising at least one target component, or at least one target material, from the tissue. Tissue to be processed may be introduced into the tissue retention volume 332 through the inlet port 304. The tissue may be pre-filtered if desired prior to being introduced into the tissue retention volume 332. The method may comprise washing tissue in the internal containment volume 330 with a wash liquid. Optionally, the washing may include centrifuging the apparatus 300. After washing, the method may comprise digesting tissue within the internal containment volume 330. After the digestion, the method may include centrifuging the apparatus 300 to prepare in the collection volume 336 a concentrate product comprising at least one target component. For example the concentrate product may comprise, or may consist essentially of, stromal vascular fraction from adipose tissue, and a target component may be stem cells from adipose tissue.

During the washing, the wash liquid may be added to the internal containment volume 330 to contact tissue within the tissue retention volume 332 and with at least a portion, preferably a majority, and more preferably most, of the wash liquid passing through the filter 312 into the filtrate volume 334. The wash liquid may wash one or more components from the tissue while retaining washed tissue in the tissue retention volume 332. The washed tissue may be retained in the tissue retention volume 332 by the filter 312. Wash liquid passing into the filtrate volume 334 may be removed from the filtrate volume 334, along with any component or components washed from the tissue. Optionally, after adding the wash liquid, the apparatus 300 may be centrifuged to facilitate a high degree of separation of the wash liquid from the tissue retained in the tissue retention volume 332. Next, the wash liquid may be removed from the filtrate volume 334 by suctioning through the suction port 302 of the apparatus 300. The washing may include multiple wash stages. During the washing, the mixing device 316 may be rotated by rotating the handle 382 to mix contents of the internal containment volume and assist the washing process.

During the digestion, an enzyme, such as for example collagenase, may be added to the internal containment volume 330 through the additional access port 372 or through the inlet port 304. During the digesting, the mixing device 316 may be rotated to assist in the digesting process.

After adding the enzyme, the digesting may comprise agitating contents of the containment volume of the apparatus 300 for a time and at a temperature sufficient for the digestion to proceed to an extent to significantly release the target component, or material, in the desired form capable of passing through the filter 312. The agitating may involve any method to agitate contents of the internal containment volume 330, including for example one or both of: (a) shaking the apparatus 300 to agitate the contents within the apparatus 300 and (b) mixing the contents within the apparatus 300 by rotating the mixing device 316 using the handle 382.

Figure 8:
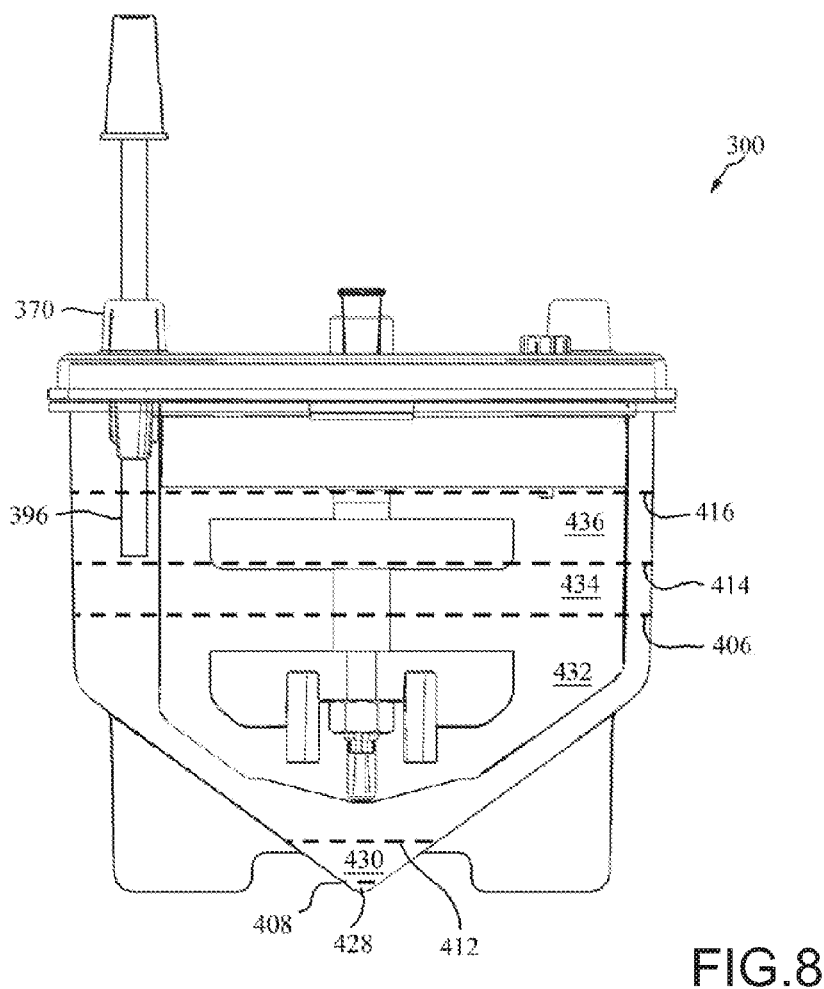
FIGS. 8-11 illustrate various operations in a method of processing tissue within a tissue collection and processing apparatus.

Post-digestion centrifuging promotes separation of the target component from the digested tissue and passage of the target component through the filter 312 for collection in the collection volume 336. The target component may include leuko stromal vascular cells (e.g., stem cells) from adipose tissue. As illustrated in FIG. 8, multiple material phases may collect within the filtrate volume 334. The first (bottom) material phase may be a small layer of red blood cells 428 located in the region of the filtrate volume 334 below the line 408. This volume below the line 408 occupies a bottom portion of the collection volume 336. The second material phase may be a stromal vascular fraction layer 430 from adipose tissue and may be located in the region of the filtrate volume 334 below the line 412 and above the line 408. As will be appreciated, the red blood cell layer 428 and the stromal vascular fraction layer 430 may not be divided by a sharp line, and the blood cell layer 428 may grade into the lower portion of the stromal vascular fraction layer 430. This volume below the line 412 and above the line 408 also occupies a portion of the collection volume 336. The stromal vascular fraction layer 430, or the stromal vascular fraction layer 430 together with the red blood cell layer 428, may be in the form of a pellet, and may be referred to as a pellet phase. A third material phase may be an aqueous layer 432 that occupies the region of the filtrate volume 334 below the line 406 and above the line 412. A fourth material phase may be a disaggregated adipose layer 434 that occupies the region of the filtrate volume 334 below the line 414 and above the line 406. A fifth material phase may be an oil layer 436 that occupies the region of the filtrate volume 334 below the line 416 and above the line 414. The separated phase layers as shown are provided to illustrate relative positioning and are not intended to represent an actual scale of the relative sizes of the phases, except that the red blood cell layer 428 and stromal vascular fraction layer 430 are contained within the collection volume 336 and the other layers extend above the collection volume. As will be appreciated, the material phases 428, 430, 432, 434 and 436 are in order of decreasing density, with red blood cell layer 428 being the most dense phase and with the aqueous layer 432, the disaggregated adispose layer 434 and the oil layer 436 all being less dense than the stromal vascular fraction layer 430.

Figure 9:
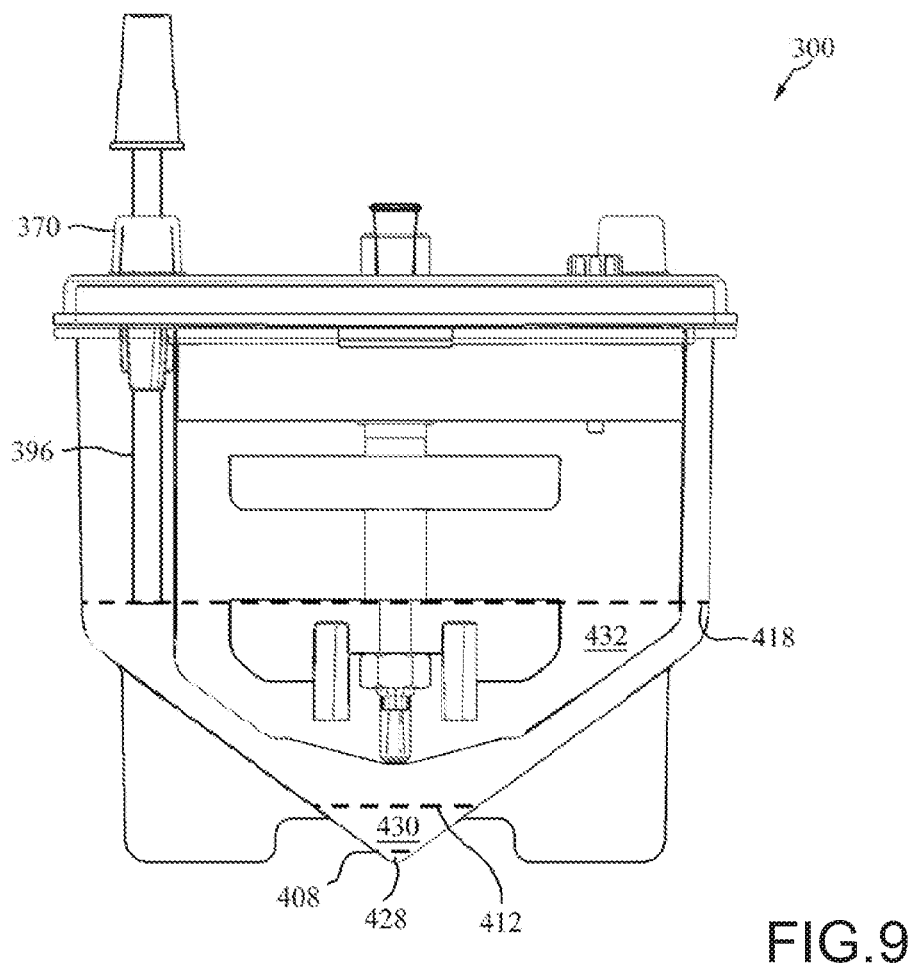

The translatable member 396 of the second suction port 370 may be employed to first remove the oil layer 436, then to remove the disaggregated adipose layer 434, and then to remove the aqueous layer 432. As illustrated in FIG. 8, the translatable member 396 may be positioned such that the end of the translatable member 396 is disposed within the oil layer 436. Suction applied to the translatable member 396 will remove fluid. As fluid is removed, the translatable member may be lowered to remove additional fluid down to a desired level, which may be removal of all or most of layers 436, 434 and 432. For example, once the oil layer 436 has been removed, the translatable member 396 may be lowered into the disaggregated adipose layer 434 and then the aqueous layer 432 for sequential removal of these layers. FIG. 9 illustrates the aqueous layer 432 partially removed (after already removing the top layers 436 and 434) such that the top of the aqueous layer 432 is at line 418. As another example, the translatable member 396 may be initially inserted to the position shown in FIG. 9 and suction applied until a portion of the aqueous layer 432 is removed and also the disaggregated adipose layer 434 and oil layer 436 are removed above line 418, resulting in the arrangement of FIG. 9.

Figure 10:
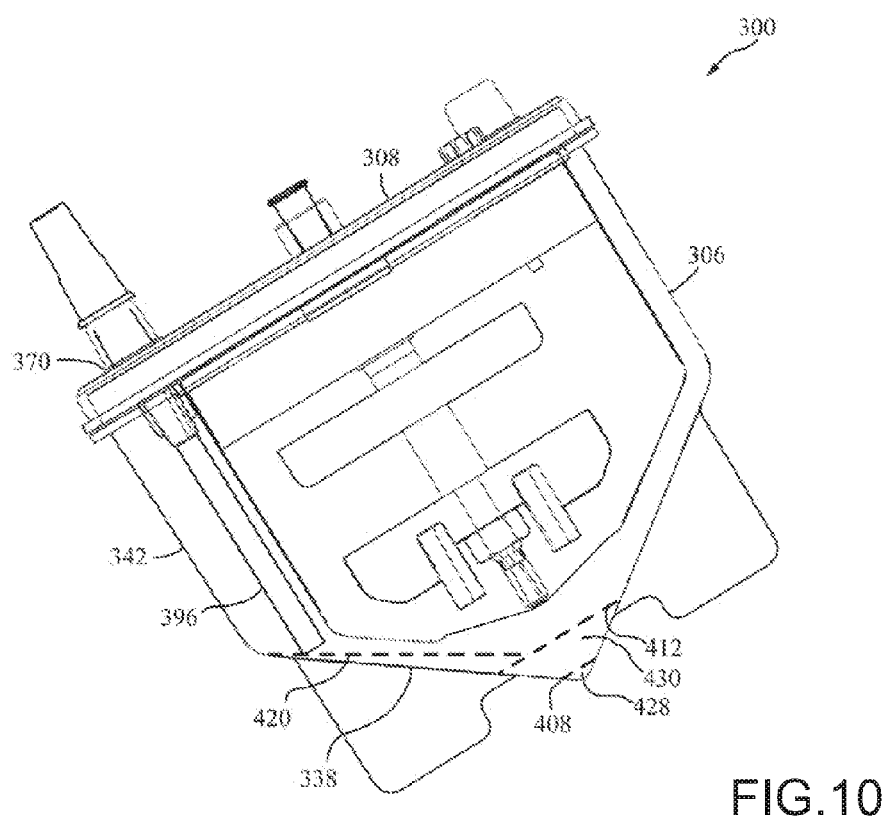
Figure 11:
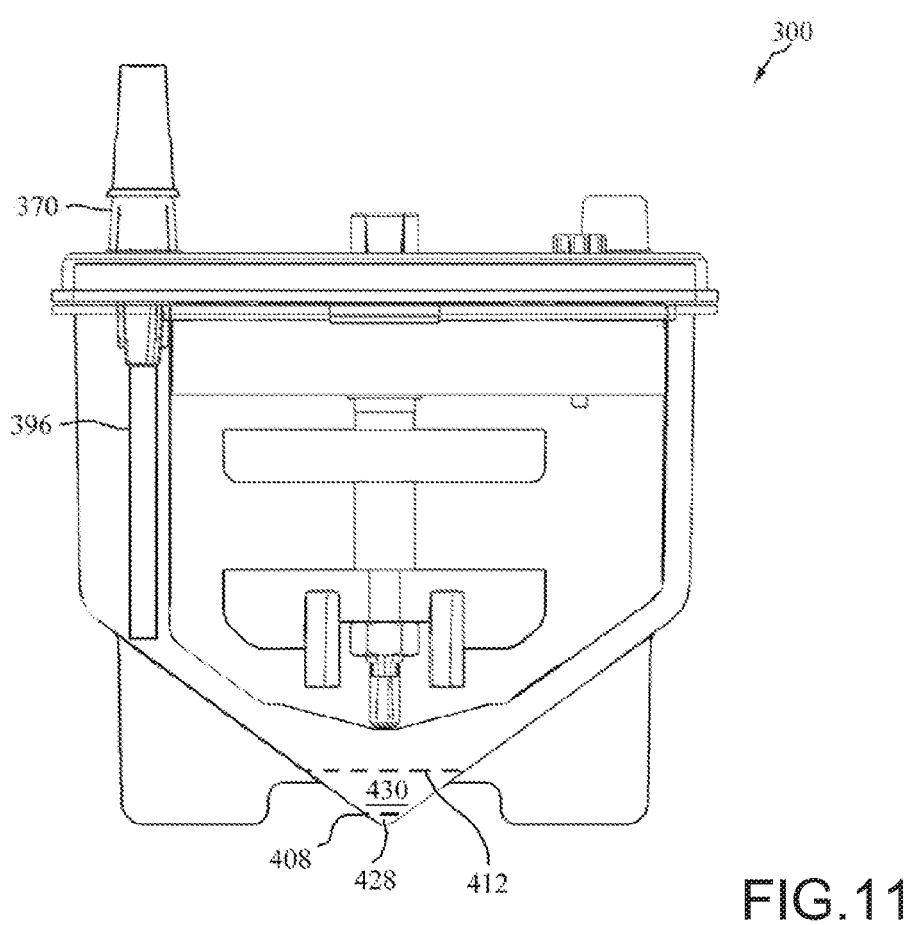

Once fully inserted into the filtrate volume 334, the translatable member 396 may not be operable to remove a portion of the aqueous layer 432 while the apparatus is in the collection orientation. Accordingly, a user may gently tilt the apparatus 300 as illustrated in FIG. 10 to further remove the aqueous layer 432. As illustrated, the stromal vascular fraction layer 430 below the line 412 may form a pellet which may retain its position as the apparatus 300 is tilted. This attribute of the pellet allows the apparatus 300 to be tilted such that the aqueous layer 432 flows laterally toward the translatable member 396 disposed proximate to the interface between the tapered wall portion 338 of the shell 306 and the straight wall portion 342 of the shell 306 as illustrated by line 420 in FIG. 10. Such tilting can allow suction to be applied to the aqueous layer 432 without the suction substantially affecting the stromal vascular fraction layer 430, which remains in place and stationary relation to the container. Once the aqueous layer 432 has been satisfactorily removed, the apparatus 300 may be returned to its collection orientation, as shown in FIG. 11, for removal of the stromal vascular fraction layer 430 from the collection volume 336.

To remove material of the pellet phase after the less-dense material phases have been removed from above the pellet phase, the hypodermic needle 392 may be inserted into the collection volume 336 from the syringe 394 as illustrated in FIG. 6 and a diluent fluid (e.g., suspension liquid) may be injected into the collection volume 336 such that the diluent fluid, stromal vascular fraction layer 430 and the layer of red blood cells 428 together occupy at least a portion of the collection volume 336, and are preferably limited to the collection volume 336. After injection of the diluent fluid, a user may gently tap the apparatus 300 against a hard surface to cause the diluent fluid to mix with the stromal vascular fraction and the layer of red blood cells. A second hypodermic needle may then be inserted through the lumen 374 and the diluent/stromal vascular fraction/red blood cell mixture may be removed from the apparatus 300, to complete the selective removal of material of the pellet phase from the container 322 relative to other, less-dense material phases.

An alternative technique to remove material of the pellet phase after the less-dense material phases have been removed from above the pellet phase, is to insert the hypodermic needle 392 such as shown in FIG. 6 into the pellet phase. The pellet phase may then be directly aspirated through the hypodermic needle 392 into the syringe 394, to complete selective removal of material of the pellet phase from the container 322 relative to the other, less-dense material phases. In this way, the material of the pellet phase may be removed from the container 322 without suspending material of the pellet phase in a suspension liquid.

As a further processing alternative, the material of the pellet phase (red blood cells layer 428 and stromal vascular fraction layer 430) may be removed from the container 322 without first removing the less-dense material phases (the aqueous layer 432, disaggregated adipose layer 434 and oil layer 436), or at least without removing all of those less-dense material phases. For example, a hypodermic needle (similar to FIG. 6) may be inserted through the lumen 374 with the distal tip of the needle disposed in the pellet phase and the material of the pellet phase may then be directly aspirated through the hypodermic needle and into a syringe in fluid communication with the hypodermic needle. This technique may permit selective removal of the material of the pellet phase from the container 322 without first removing the less dense-material phases and without suspending the material of the pellet phase in a suspension liquid. After removal of the material of the pellet phase, the less-dense material phases may remain inside the container 322. Removal by such a technique significantly simplifies processing, because the processing associated with removing the less-dense material phases (including tapping the container) may be eliminated, reducing potential processing errors and potential loss of target cells to adhesion to container or equipment surfaces.

Figure 12:
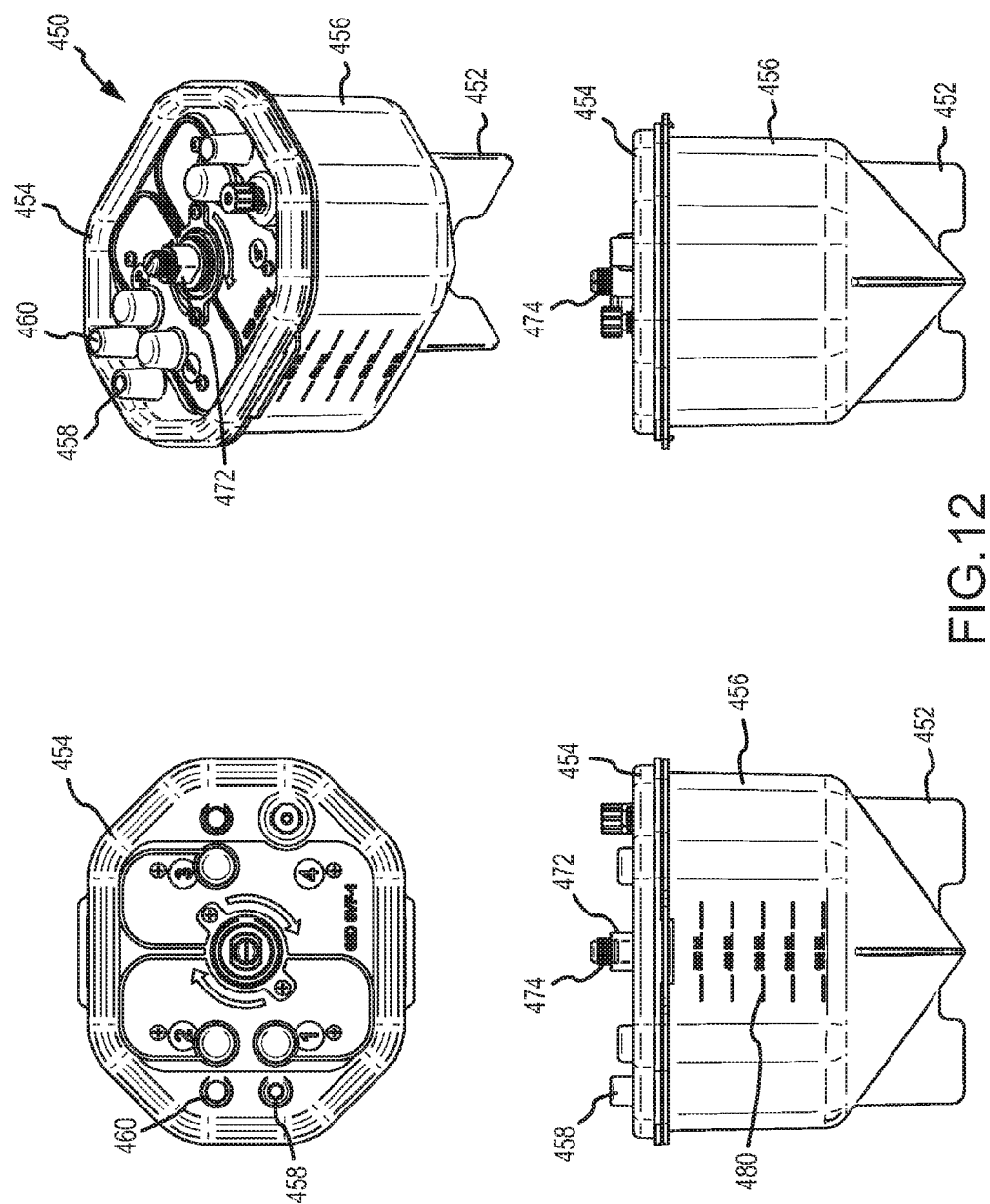
FIG. 12 shows top, perspective, side and end views of another embodiment of a tissue collection and processing apparatus.
Figure 13:
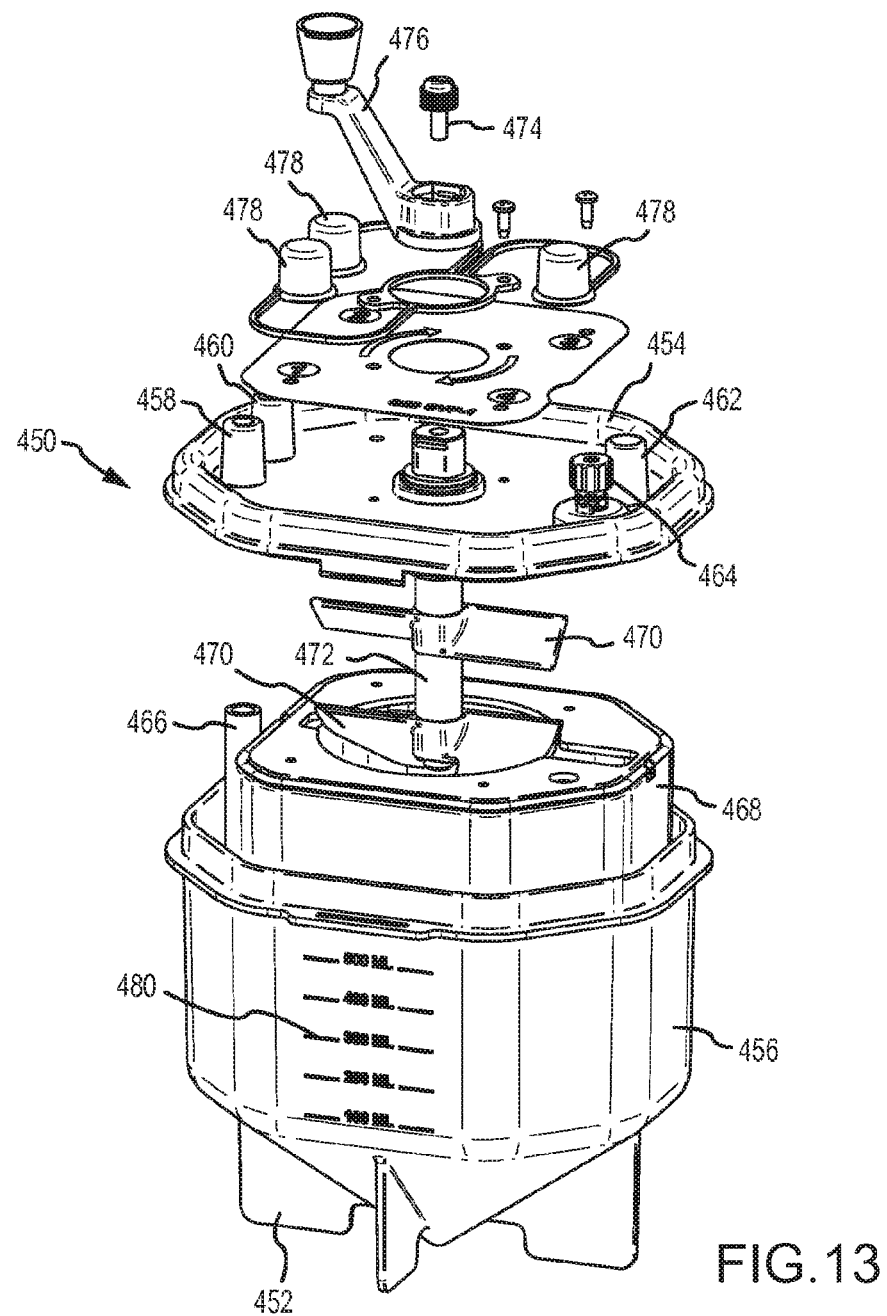
FIG. 13 shows an exploded view of the same tissue collection and processing apparatus as FIG. 12.

Referring now to FIGS. 12 and 13, a further embodiment is shown for a tissue collection and processing apparatus. As shown in FIGS. 12 and 13, a tissue collection and processing apparatus 450 has a collection orientation in a freestanding, upright position as supported by base supports 452. The apparatus 450 includes a lid 454 covering a bowl-like shell 456, which make up a container having an internal containment volume under the lid within the shell. The apparatus includes a first suction port 458, a second suction port 460, an inlet port 462 and an auxiliary access port 464, which may be generally as described for similar features of the apparatus 300 described with respect to FIGS. 1-11.

The first suction port 458 is connected with a suction conduit 466 extending from the first suction port 458 to within a tapered portion of an internal containment volume of the apparatus 450. The second suction port 460 is adapted to receive a translatable suction conduit, similar to the translatable member 396 described with respect to FIG. 7. The apparatus 450 includes a filter 468 suspended from the lid 454 and which divides the internal containment volume in the apparatus between a tissue retention volume disposed inside the filter 468 and a filtrate volume disposed on the other side of the filter 468. The apparatus 450 includes a rotatable mixer disposed within the filtrate volume that includes propellers 470 connected to a rotatable shaft 472, which may be rotated to operate the rotatable mixer and cause the impellers 470 to mix and circulate fluid within the internal containment volume of the apparatus 450. The rotatable shaft 472 includes an internal lumen that extends from a proximal end outside of the container of the apparatus to a distal end in the tissue retention volume, to permit access into the internal containment volume in a manner similar to that discussed previously for the apparatus 300 shown in FIGS. 1-7. A removable plug 474 may be disposed in a proximal end of the lumen for sealing the lumen when the lumen is not in use. The rotatable shaft includes a handle interface which may be interfaced with a hand-manipulable handle 476 (FIG. 13) to operate the rotatable mixer. The apparatus 450 includes attached caps 478 which may be used to cap the first suction portion 458, second suction port 460 and inlet port 462 as needed, such as to seal the container for transportation between processing locations or during agitation on a warmer-shaker during digestion operations. The apparatus 450 is operable substantially in the same way as described previously for the apparatus 300 shown in FIGS. 1-11. The apparatus 450 includes volume gradation markings 480 that indicate the volume contained within the tissue retention volume (within the filter 468) up to different elevations of the container 450 when in the access orientation.

Figure 14:
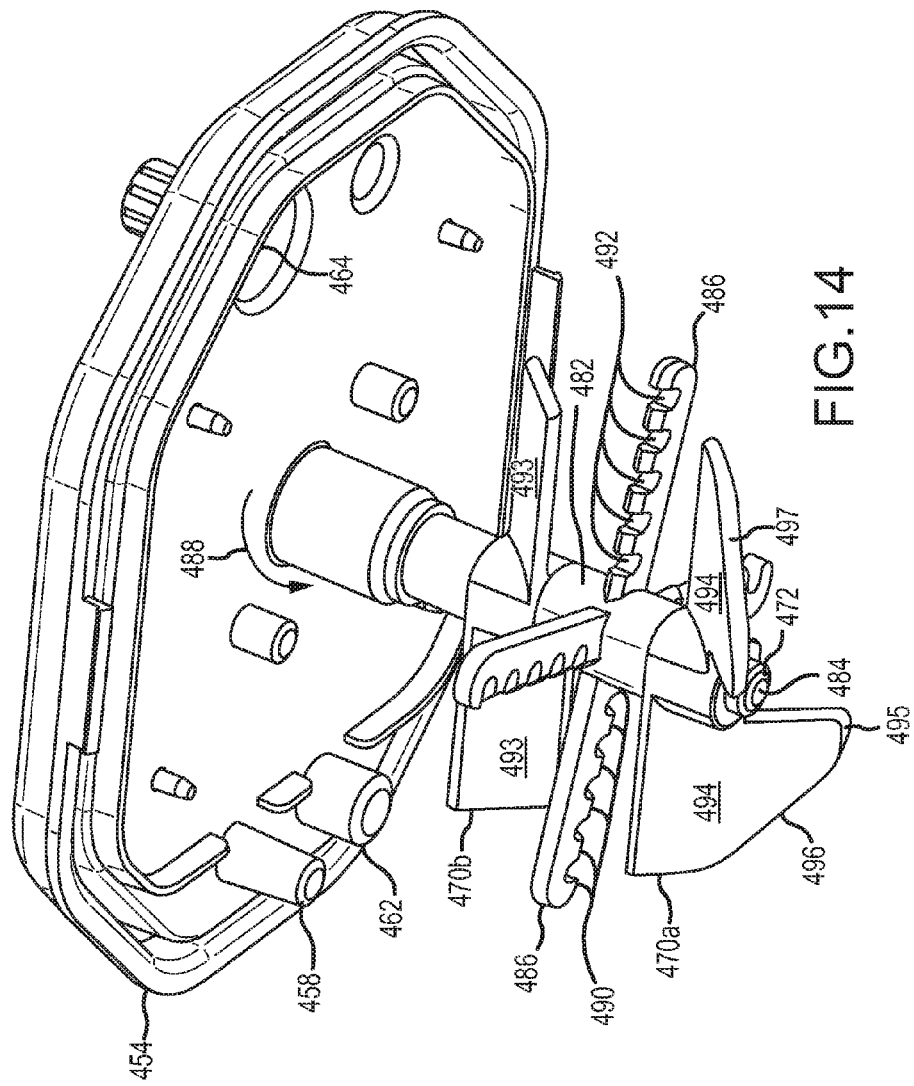
FIGS. 14 and 15 illustrate a portion of another embodiment of a tissue collection and processing apparatus including a rotatable tissue collector.
Figure 15:
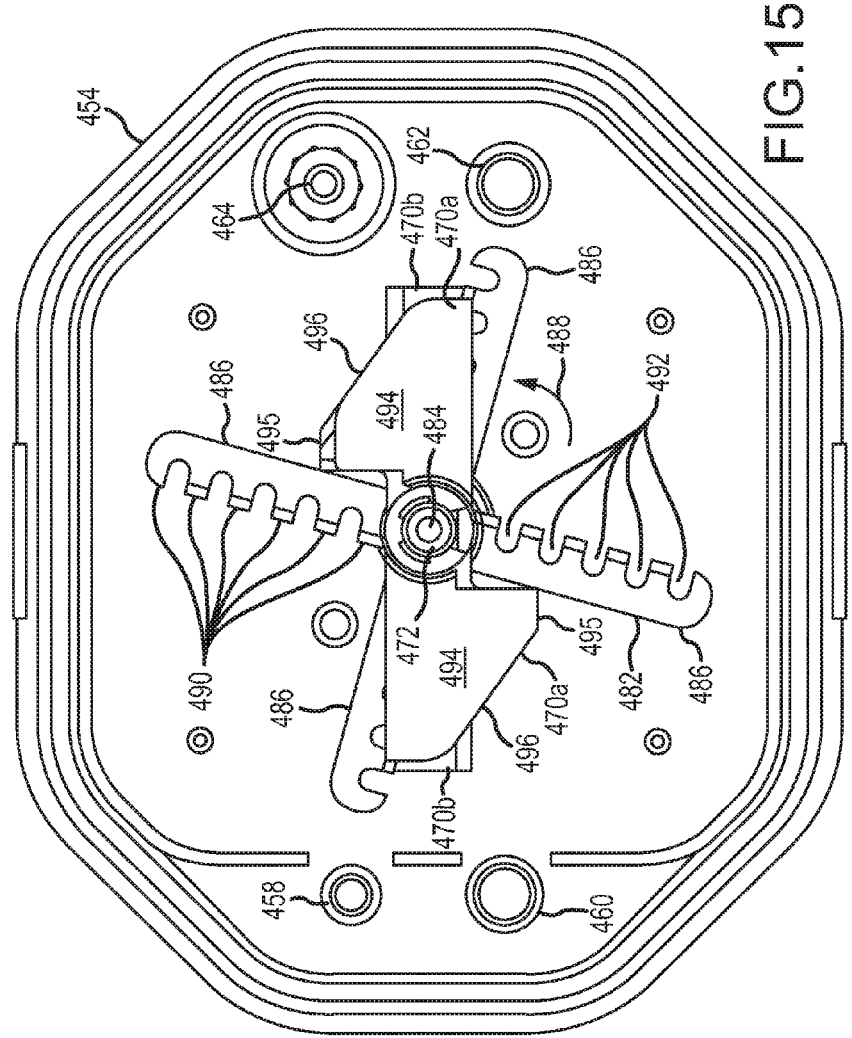
Figure 16:
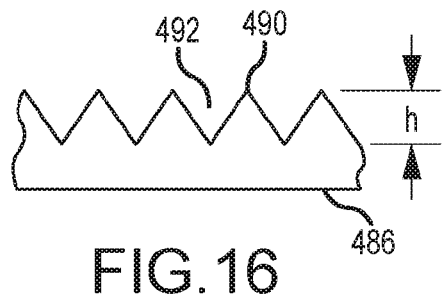
FIG. 16 illustrates an example tooth configuration for a toothed member for a rotatable tissue collector.
Figure 21:
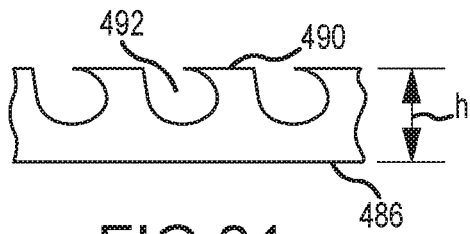
FIG. 21 illustrates another example tooth configuration for a toothed memeber for a rotatable tissue collector.
Figure 22:
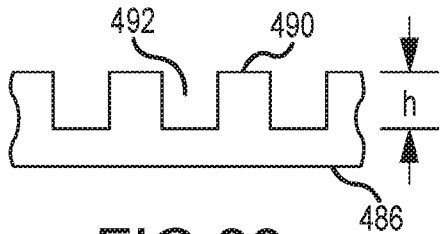
FIG. 22 illustrates another example tooth configuration for a toothed memeber for a rotatable tissue collector.

Reference is now made to FIGS. 12-15. FIGS. 14 and 15 show a configuration for an alternative rotatable assembly that may be disposed in the tissue retention volume of a tissue collection and processing apparatus, and for convenience of description and brevity will be discussed in the context of an alternative embodiment of the apparatus 450 shown in FIGS. 12 and 13. Reference numerals used in FIGS. 14 and 15 are the same as used in FIGS. 12 and 13 for like features. FIGS. 14 and 15 show a rotatable tissue collector 482, which may alternatively be referred to as a tissue comb or more particularly as a stringy-tissue comb. As shown in FIGS. 14 and 15, the lid 454 has the first suction port 458, second suction port 460, inlet port 462 and auxiliary access port 464 providing access through the lid 454 into the internal containment volume of the container of the apparatus 450. The mixing propellers 470 are shown mounted on the rotatable shaft 472. For convenience of description, in FIGS. 14 and 15 the lower propeller is designated 470a and the upper propeller is designated 470b. Also shown is a terminal end of a lumen 484 that passes through the rotatable shaft 472 to provide access from above the lid 454 into the internal containment volume of the container of the apparatus 450.

As shown in FIGS. 14 and 15, the tissue collector 482 is disposed on the shaft 472 intermediate between the propeller 470a and propeller 470b. The propellers 470 may alternatively be referred to as impellers or mixing impellers. Also shown in FIGS. 14 and 15 is a rotational direction 488 represented by an arrow and showing a rotational direction for rotating the shaft 472 to rotate the propellers 470 and the tissue collector 482 during one possible operation of the apparatus. The rotational direction 488 corresponds with the directional arrows on a plate shown in FIG. 13 that is visible at the top of the device to show direction of rotation for operation of the apparatus 450.

The tissue collector 482 includes four tissue collection members 486, which may also be referred to as tissue collection blades. The tissue collection members 486 each includes a plurality of teeth 490 and open spaces 492, configured with an open space 492 located between each pair of adjacent teeth 490. The tissue collection members 486 thus have a toothed configuration that facilitates engagement and collection of stringy tissue, such as collagen, when the tissue collector 482 is rotated in the rotation direction 488, such as may be affected by rotating the rotatable shaft 472 using the handle 476. The open spaces 492 may alternatively be referred to as slots or recesses, and the open spaces 492 provide locations for stringy tissue engaging with the tissue collector 482 to be collected and retained. As stringy tissue collects in the open spaces 492, the stringy tissue may also tend to wrap around the rotatable shaft 472 to assist retention of the stringy tissue. By collecting and retaining the stringy tissue using the tissue collector 482, plugging of the filter 468 may be significantly reduced because less of the stringy tissue is available to collect on and plug the filter 468. The teeth 490 each have a top (maximum protrusion of a tooth 490 relative to the bottom of an adjacent open space 492) that is thus disposed toward a leading edge of the corresponding member 486 when the tissue collector 482 is rotated in the rotational direction 488. The bottom of an open space 492 may be the most recessed portion of the open space relative to the top of an adjacent tooth 490 as defined by the surface geometry of the member 486. In the configuration shown in FIGS. 14 and 15, each member 486 includes six teeth 490 and five open spaces 492.

With continued reference to FIGS. 12-15, features of one or both of the propellers 470 may be configured to assist collection of stringy tissue by the tissue collector 482 and to reduce potential for plugging of the filter 468. As shown in FIGS. 12-15, one or both of the propellers 470 may have pitched blades that direct flow of fluid from the respective propeller 470 in an axial direction relative to the axis of rotation of the rotatable shaft 472. As shown in FIGS. 14 and 15, the configuration of the bottom propeller 470a may include impeller blades 494 that are pitched at an angle that will propel fluid flow in an upper axial direction along the rotatable shaft 472 directed toward the tissue collector 482 when the rotatable shaft 472 is rotated in the rotational direction 488. This type of upward pumping action by the propeller 470a may assist in moving stringy tissue away from the filter 468 and toward the tissue collector 482 to engage and collect on the members 486. In similar manner, as shown in FIGS. 14 and 15, the top propeller 470b may have pitched blades 493 that propel fluid flow in an axial direction upward toward the underside of the lid 454 and away from the tissue collector 482 when the rotatable shaft 472 is rotated in the rotational direction 488. This upward pumping action by the propeller 470b may assist in pulling tissue through the tissue collector 482 to promote collection of stringy tissue by the members 486. As a design enhancement, the tissue collection members 486 may extend in an radial direction outward from the axis of the rotatable shaft 472 to a greater distance than either one of or both of the blades of the propellers 470a,b. In particular, it is preferred that the members 486 may extend in a radial direction a distance that is beyond the radial distance of a maximum extent of the blades 494 of the bottom propeller 470a, and in a further enhancement the members 486 may extend in a radial direction farther than a maximum extent of the blades 493, 494 of either of the propellers 470a and 470b. In this way the members 486 may be configured to collect stringy tissue beyond the radial extent of one or both of the propellers 470a,b.

In one enhancement, one or more of the blades 494 may be configured to scrape at least a portion of the filter 468 when the rotatable shaft 472, and thus also the bottom propeller 470a, is rotated in the rotational direction 488. In the configuration shown in FIGS. 12-15, such scraping of the filter 468 may be accomplished by configuring a bottom edge portion 495 and/or slanted edge portion 496 of a blade 494 to contact and scrape surfaces of the filter 468. In that regard, the slanted edge portion 496 of a blade 494 may be configured to correspond with and contact a corresponding tapered portion of the filter 468. A leading edge of the blade 494 may have a tapering width to assist in scraping tissue away from the surface of the filter 468. For example, the configuration of the blade 494 as shown in FIG. 14 includes a beveled surface 497 toward a leading edge of the slanted edge portion 496 that may help to lift tissue away from the filter 468 when the lower propeller 470a is rotated in the rotational direction 488.

As shown in FIGS. 14 and 15, the teeth 490 of the members 486 may have beveled surfaces toward a leading edge that facilitate more easy rotation of the tissue collector 482 through tissue that may be disposed in the tissue retention volume of the container of the apparatus 450.

A rotatable tissue collector, for example as shown in FIGS. 14 and 15, may preferably be used in combination with at least one mixing impeller and/or in combination with at least two mixing impellers (as shown in example of FIGS. 14 and 15). Alternatively, the tissue collector may be used by itself and not in combination with any separate mixing impeller. When a separate mixing impeller is used, one or more such separate mixing impeller may include one or more pitched blades (e.g., blades 494, 493 of propellers 470a,b of FIGS. 14 and 15) that impart axial flow for mixing, or one or more such separate mixing impeller may include one or more unpitched blades that impart radial flow (e.g., mixing members 320 of FIG. 4). When a rotatable tissue collector is used alone, without any separate mixing impeller, the tissue collector by itself may serve also as a rotatable mixer with the tissue collection members also acting as mixing members to mix contents within a tissue retention volume. In a preferred implementation, a rotatable tissue collector is used in combination with at least one mixing impeller. When only one mixing impeller is present, it is more preferred to dispose the mixing impeller at a lower elevation on a rotatable shaft (e.g., propeller 470a of FIGS. 14 and 15) although an alternative arrangement is to include the mixing impeller at a higher elevation on a rotatable shaft (e.g., propeller 470b of FIGS. 14 and 15). A preferred configuration is for each mixing impeller and tissue collector to be coaxial and connected to and rotatably driven by a single rotatable shaft, although such a single shaft arrangement is not required. For instance, one or more mixing impellers may be connected to and driven by one or more rotatable shafts separate from a rotatable shaft that drives a rotatable tissue collector. A tissue collection and processing apparatus may have multiple rotatable tissue collectors, which may have the same or different configurations and may be driven by the same or different rotatable shafts.

The teeth and adjacent open spaces on tissue collection members of a rotatable tissue collector may have a variety of configurations. It is not necessary that the teeth be of the same height or configuration or that the open spaces be of the same size or configuration, either on the same tissue collection member or on different tissue collection members.

Figure 23:
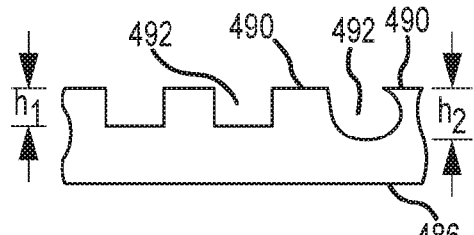
FIG. 23 illustrates another example tooth configuration for a toothed memeber for a rotatable tissue collector.
Figure 24:
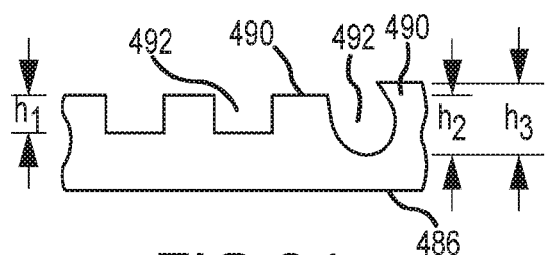
FIG. 24 illustrates another example tooth configuration for a toothed memeber for a rotatable tissue collector.
Figure 16A:
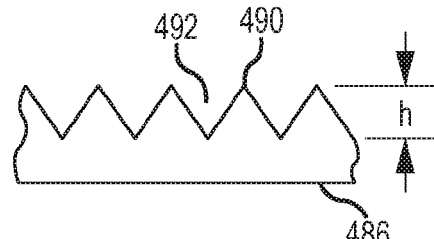
Figure 16B:
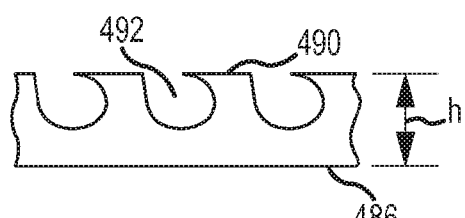
Figure 16C:
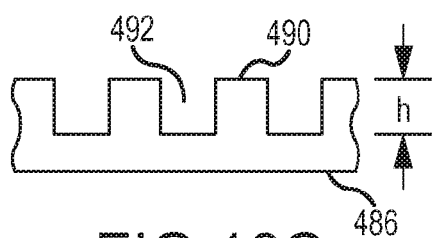
Figure 16D:
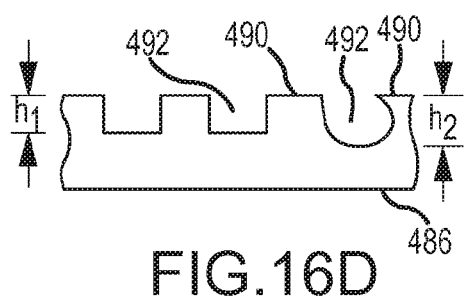
Figure 16E:
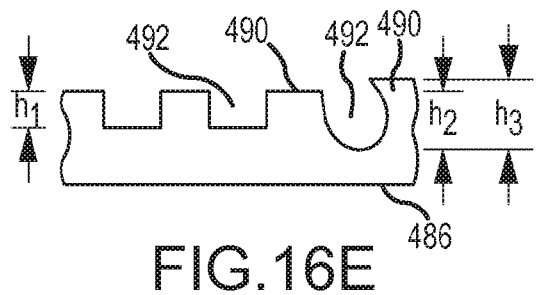

Reference is made to FIGS. 16 and 21-24 showing some example configurations for open spaces and teeth for a tissue collection member. Reference numerals corresponding with the tissue collection members, teeth and open spaces are the same as used in FIGS. 14 and 15, for convenience of description. FIGS. 16 and 21-24 show five example configurations showing some examples for different configurations for teeth 490 and open spaces 492 for a tissue collection member 486. Examples of FIGS. 16, 21 and 22 all have teeth 490 that have a height h (distance between the top of a tooth 490 and the bottom of an adjacent open space 492) that is equal for all teeth 490. The example of FIG. 23 shows a configuration in which some teeth 490 have a greater height $h_2$ than the height $h_1$ of some other teeth 490. The example of FIG. 24 shows a configuration with three different tooth heights ($h_1$, $h_2$, $h_3$). Examples of FIGS. 23 and 24 also show configurations in which not all of the teeth 490 and the open spaces 492 are configured with the same geometry.

Figure 17:
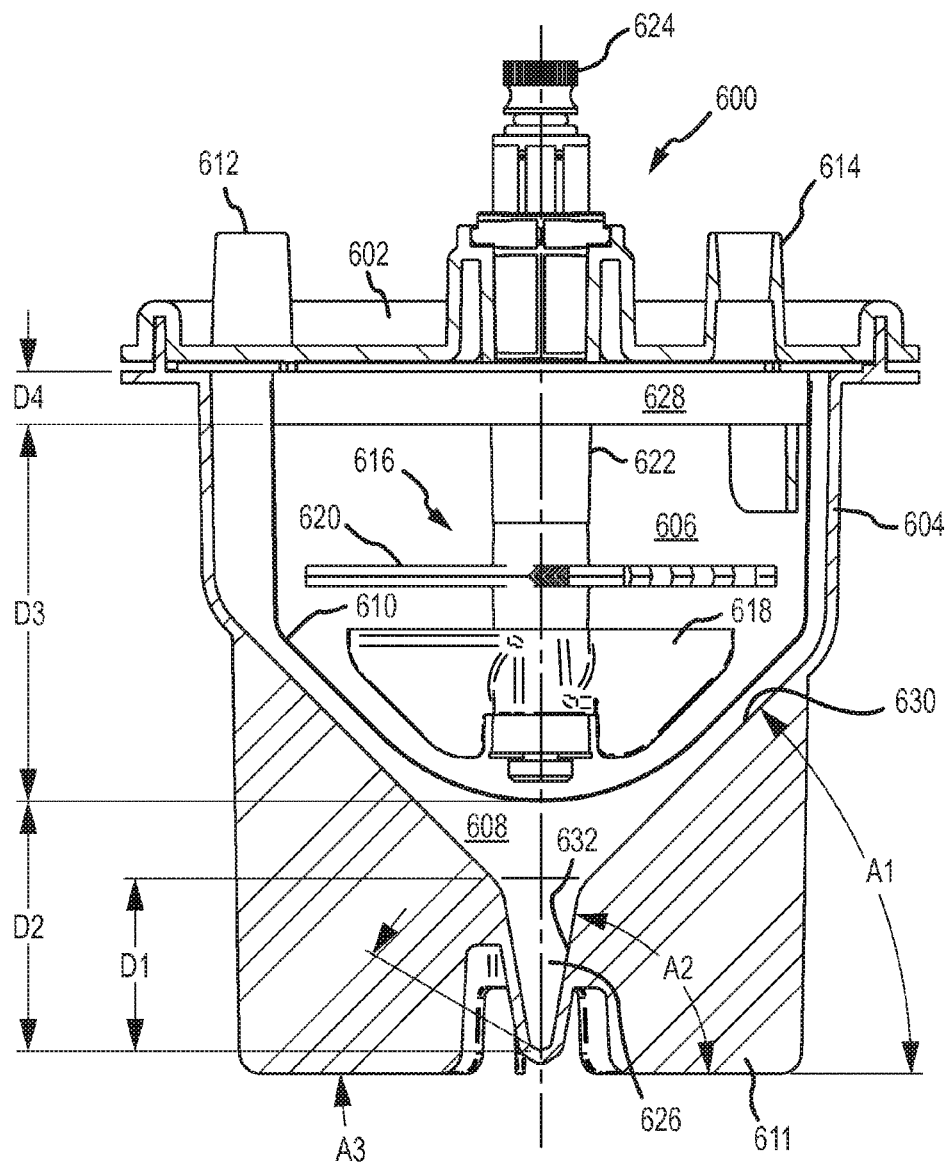
FIG. 17 shows a sectional view illustrating some features of another embodiment of a tissue collection and processing apparatus.

Reference is made to FIG. 17, which shows another embodiment for a tissue collection and processing apparatus.

FIG. 17 shows an apparatus 600 including a lid 602 and a shell 604 that form a container having an internal containment volume including a tissue retention volume 606 and a filtrate volume 608 disposed on different sides of a filter 610. The apparatus 600 is shown in an access orientation as it would be supported by base supports 611 that are integrally formed with the shell 604. A suction port 612 is in fluid communication with the filtrate volume 608 and through which material may be removed from the filtrate volume 608. An inlet port 614 is provided for introducing tissue or other material into the tissue retention volume 606. The apparatus 600 may include additional access ports parts (e.g., additional suction port, auxiliary port), such as described for previous embodiments. The apparatus 600 includes a rotatable assembly 616 including a mixing impeller 618 and a tissue collector 620. The mixing impeller 618, tissue collector 620 and a spacer 622 are mounted on a rotatable shaft (not shown) that extends from above the container through the lid 602 and into the tissue retention volume 606. The rotatable shaft includes a central lumen that extends through the rotatable shaft from outside the container and opens at the bottom of the mixing assembly near the bottom portion of the tissue retention volume 606 just above the filter 610. The lumen is accessible by removing a cap 624. The lid 602, shell 604, tissue retention volume 606, filtrate volume 608, filter 610, base supports 611, suction port 612, inlet port 614, rotatable shaft, mixing impeller 618 and tissue collector 620 may have any design features or configurations as described previously in relation to corresponding features of the apparatus described in any of FIGS. 1-16 and 21-24. The apparatus 600 does, however, include a pellet well 626 at the bottom of the filtrate volume 608, as discussed further below.

In some preferred implementations, the tissue collector 620 may have a design similar to the corresponding tissue collector described with respect to FIGS. 14-16 and 21-24 and the mixing impeller 618 may be configured with pitched blades for producing axially upward flow toward the tissue collector 620 when the rotatable shaft is rotated in an appropriate direction. The blades of the mixing impeller 618 may beneficially be designed with portions that scrape the filter 610 as the rotatable shaft 616 is rotated, in a manner similar as described above with respect to FIGS. 14-16 and 21-24. The lumen through the rotating shaft may be aligned with a collection volume located in the filtrate volume 608 below the bottom of the filter 610, and may provide access for convenient removal of processed material from the pellet well 626 in the collection volume located below the filter 610.

Various example dimensions are shown for the apparatus 600. A first height dimension $D_1$ shows the vertical dimension from the bottom of the collection volume at a nadir of the filtrate volume 608 to a top elevation of the collection volume occupied by the pellet well 626. Second height dimension $D_2$ shows the vertical dimension from the bottom to the top of the collection volume that is below the filter 610. Third height dimension $D_3$ shows the vertical dimension from the bottom of the filter 610 to the bottom of a skirt 628 from which the filter 610 is suspended. Fourth height dimension $D_4$ shows the vertical extent of the skirt 628. Angle $A_1$ is an angle between horizontal and a first tapered interior wall surface 630 of the container that defines at least a portion of the filtrate volume 608, including defining at least a portion of the collection volume. Angle $A_2$ is an angle from horizontal to a second tapered interior wall surface 632 of the container that defines at least a portion of the pellet well. Angle $A_3$ is an angle between horizontal and a third tapered interior wall surface of the container that defines at least a bottom portion of the pellet well 626. Example dimensions for one example implementation for the embodiment of the apparatus 600 includes 25.7 millimeters for $D_1$, 37.1 millimeters for $D_2$, 55.9 millimeters for $D_3$, 7.9 millimeters $D_4$, 45° for $A_1$, 80° for $A_2$, and 30° for $A_3$. Such an example may be designed for example to include an internal containment volume of about 270 cubic centimeters and a volume in the pellet well 626 of about 1.2 cubic centimeters, and with the filtrate volume 606 configured to accommodate processing of about 110 cubic centimeters of adipose tissue in the tissue retention volume 606 for preparation of a pellet phase including leuko stromal vascular fraction concentrate that may fill or nearly fill the pellet well 626.

Figure 18:
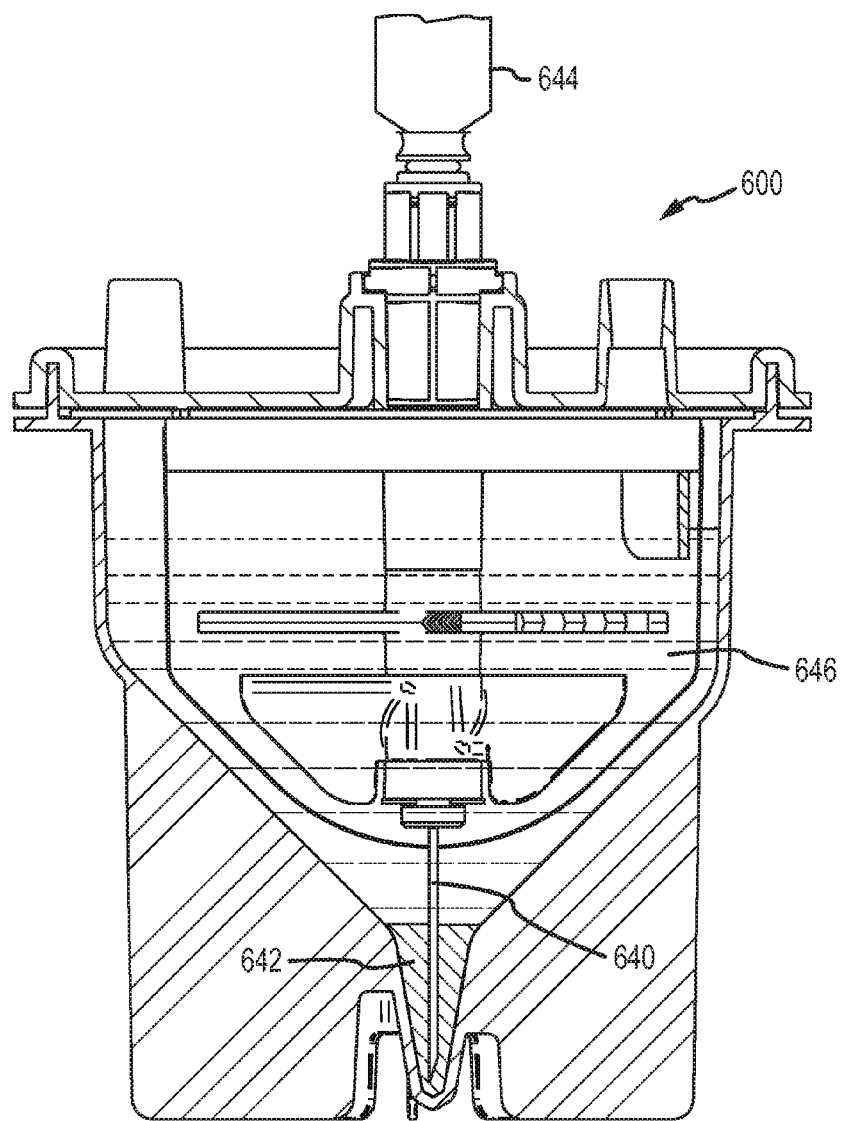
FIG. 18 illustrates the same tissue collection and processing apparatus as FIG. 17 showing a needle inserted into a pellet well to aspirate pellet phase material.

The location and configuration of the pellet well 626 in the embodiment of the apparatus 600 shown in FIG. 17 facilitates direct aspiration of material of a pellet phase that may collect in the pellet well 626 by providing a relatively deep and narrow chamber that helps facilitate effective aspiration of the pellet phase material without also aspirating large quantities of overlying material from less-dense material phases that may form during centrifuge processing. FIG. 18 shows the apparatus 600 of FIG. 17 in which a hypodermic needle 640 is inserted through the lumen of the rotatable shaft to access pellet phase material 642 from above for direct aspiration of the pellet phase material 642 from the pellet well 626 through the hypodermic needle 640 to outside of the container and into a syringe 644. Such direct aspiration of the pellet phase material 642 may be performed without first removing less-dense material 646 from above the pellet phase material 642 and without suspension of the pellet phase material 646 in a suspension liquid. The syringe 644 may be preloaded with a quantity of dispersion medium that mixes with and disperses aspirated pellet phase material as it is introduced into the syringe 644. This may help prevent clumping of the pellet phase material in the syringe. The resulting mixture of pellet phase material and dispersion medium may be removed and further processed to prepare a composition for administration to a patient or the mixture may be directly administered to a patient as a delivery composition, such as by injection into a patient in the vicinity of a joint to treat for osteoarthritis at the joint. If a mixture in the syringe is removed from the syringe 644 for further processing, the mixture may be centrifuged to separate pellet phase material and suspension liquid and the separated pellet phase material may be recovered and formulated with other components in a delivery composition, which may for example include a scaffold material or may include dispersion in a new dispersion medium with properties and at a volume desired for a particular treatment application. Any of the wall surfaces defining at least a portion of any of the first tapered portion, second tapered portion and third tapered portion may have inclined planar geometry with a constant angle of inclination, as shown in FIGS. 17 and 18 for angles $A_1$, $A_2$ and $A_3$ or may have a curved geometry with a changing angle of inclination. When such a surface has a curved geometry, the respective angle, may be, may be the angle of inclination of a line tangent to a point on the curved geometry.

Figure 19:
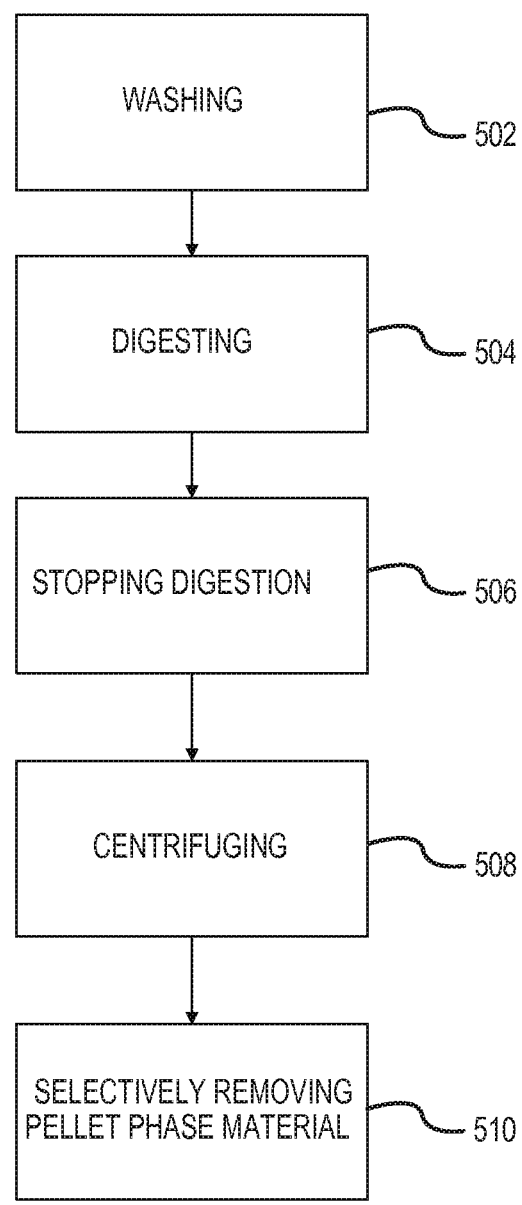
FIG. 19 is a generalized process block diagram of an embodiment of a method of processing adipose tissue.

FIG. 19 is a generalized process block diagram illustrating one embodiment of a method involving multi-step processing within a portable container, such as for example using a tissue collection and processing apparatus as previously described. As shown in FIG. 19, the method includes a washing step 502, during which adipose tissue disposed within a portable container is washed to remove contaminants from the adipose tissue. Contaminants that may be associated with the adipose tissue include for example blood, free lipids, small particles and debris and other materials that may have been collected with the adipose tissue or result from degradation during a tissue collection operations.

The washing 502 may include one or multiple wash cycles during which adipose tissue is washed with wash liquid within the container. The wash liquid, for example, may be a buffer solution, such as Lactated Ringer's solution or Hank's Balanced Solution, and may have additional additives, such as one or more of an anti-clotting agent, an antibiotic and an antifungal. An anti-clotting agent may beneficially prevent coagulation of blood that may be present, and may assist effective washing of blood from the adipose tissue. Antibiotics and antifungals may help protect against problems associated with inadvertent outside contamination of the adipose tissue within the container. Such a wash liquid may also include one or more additional buffering agents, such as glycine. One preferred material for use as an anti-clotting agent is heparin.

During a wash cycle, the wash liquid is mixed with the adipose tissue in the container and then preferably substantially all of the wash liquid with washed contaminants from the adipose tissue is removed from the container from a filtrate volume on a first side of a filter within the container while retaining the washed adipose tissue in a tissue retention volume of the container on a second side of the filter.

The washing may include any of the features discussed above.

After the washing 502, the washed adipose tissue in the container is subjected to a digesting step 504. Digestion medium, such as comprising a collagenase enzyme solution, is added to the container to contact the washed adipose tissue. The digestion medium may for example be added in a volume ratio of in a range of from 0.6:1 to 2:1 digestion medium:adipose tissue. The digestion medium may contain collagenase enzyme, for example in an amount to provide from 150 to 300 collagen digestion units (CDU) per milliliter of catalytic volume. Catalytic volume refers to the total volume of the digestion medium and adipose tissue within the container to which the digestion medium is added. After the digestion medium is added to the container, enzymatic digestion within the container is permitted to proceed for a retention time, for example, of from 20 minutes to 50 minutes while the container is disposed in a temperature controlled environment maintained within a temperature range preferably of from 32° C. to 38° C., and with at least occasional, and preferably substantially continuous, agitation of contents to the container. The digesting step 504 may include any or any combination of the feature refinements and additional features discussed above.

The method as shown in FIG. 19 also includes a stopping digestion step 506 occurring after the digesting step 504. The stopping digestion step 506 should preferably occur no earlier than the end of the retention time for the enzymatic digestion in the temperature controlled environment, but in any event should more preferably be performed within 50 minutes following adding the digestion medium to the container during the digesting step 504. The stopping digestion step 506 includes adding a stopping reagent to the container to positively stop enzymatic activity within the container. This is important, because if enzymatic activity is not discontinued, digestion within the container may proceed to an undesirable degree in which the enzyme may destroy the viability of a significant number of the leuko stromal vascular cells.

As shown in FIG. 19, the method includes, after the stopping digestion step 506, a centrifuging step 508. The centrifuging step 508 is performed with the container disposed in a centrifuge and the centrifuge is operated to centrifuge the container to form density-separated phases within the container. These density-separated phases include a higher-density pellet phase rich in leuko stromal vascular cells, which pellet phase may form adjacent a bottom of the container. The density-separated phases also include lower-density material phases. By lower-density, it is meant that the lower-density material phases have a lower-density than the pellet phase. When the container is oriented with the pellet adjacent a bottom of the container (e.g., in an access orientation for the container), the lower-density material phases will be disposed in the container above the pellet phase. The lower-density material phases may include, in order of decreasing density, an aqueous layer, a disaggregated adipose layer (containing remnants of disaggregated adipose tissue) and an oil layer. The pellet phase is enriched in, and may be mostly or even substantially entirely comprised of, leuko stromal vascular cells (e.g., stromal vascular fraction). On a side of the pellet phase opposite the lower-density material phases may be disposed a small red blood cell phase. Provided that washing of the adipose tissue is thorough during the washing step 502, this red blood cell phase may be extremely small, and in some case may be difficult to distinguish from a bottom portion of the pellet phase. The centrifuging step 508 may include any or any combination of the feature refinements and additional features discussed above.

As shown in FIG. 19, the stopping digestion step 506 is performed after the digesting step 504 and prior to the centrifuging step 508. Such sequencing is preferred, but not required. In one variation, the stopping digestion step 506 may be performed after the centrifuging 508. However, because enzymatic digestion would continue during the centrifuging, such a variation in the sequence is not preferred, to provide better control over the timing and extent of the enzymatic digestion.

After the centrifuging step 508 has been completed, the container may be removed from the centrifuge and subjected to a step 510 of selectively removing pellet phase material. The leuko stromal vascular cells, which include stem cells, contained in the pellet phase represent a valuable product. For effective use of these valuable leuko stromal vascular cells, it is generally necessary to remove the cells from the container. This has been a significant problem in the context of using multi-step portable containers for processing that is addressable with various implementations of the invention. During the step 510, material of the pellet phase is removed from the internal containment volume of the container to outside of the container separate from the less-dense material phases. The step 510 may include any of the features as discussed above. In some processing alternatives, the pellet phase material may be directly aspirated through an aspiration tube (e.g., hypodermic needle) inserted into the pellet phase from above and material of the pellet phase may be directly aspirated from the container through the aspiration tube, for example into a syringe or other fluid receptacle located outside of the container.

Figure 20:
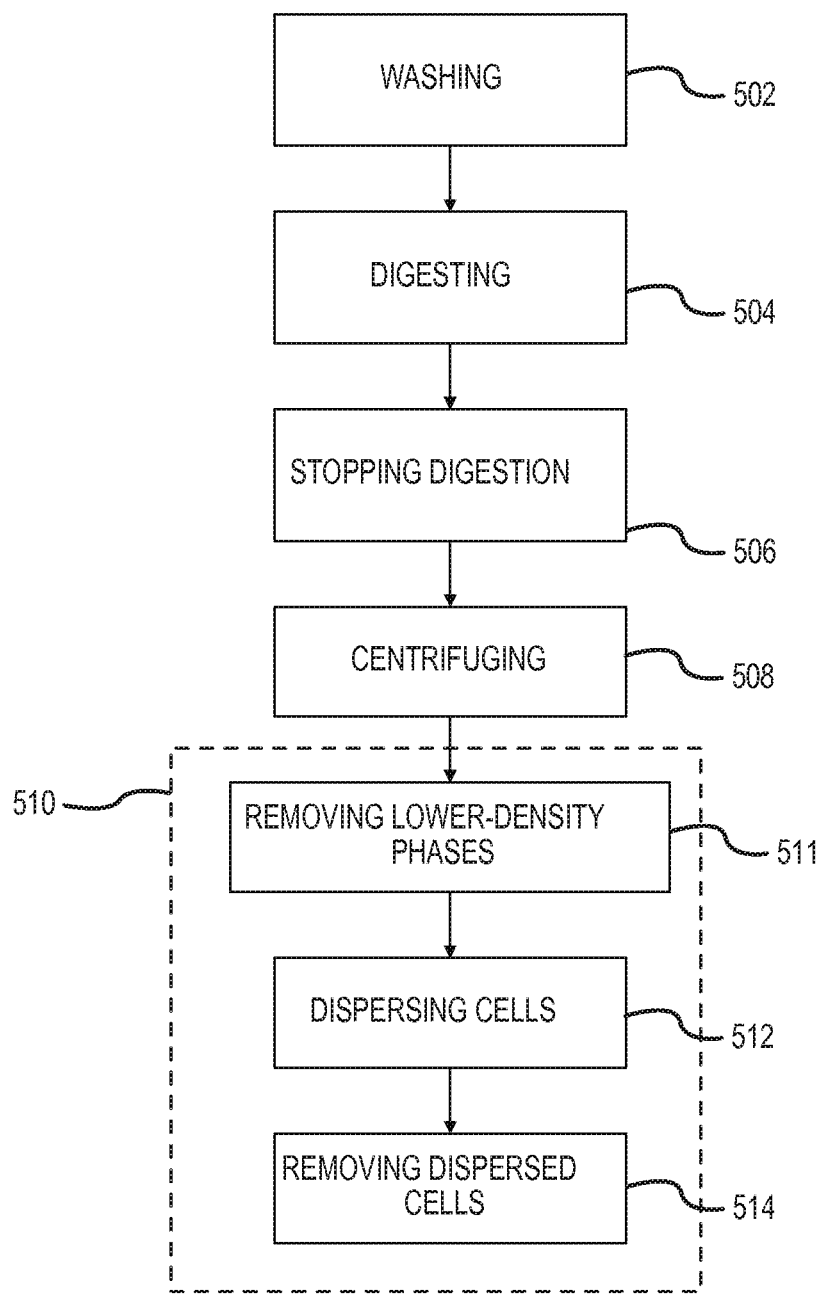
FIG. 20 is a generalized process block diagram of another embodiment of a method of processing adipose tissue.

Referring now to FIG. 20, another embodiment of implementation of a method is shown, including an alternative approach for selectively removing material of the pellet phase from the container that. The implementation shown in FIG. 20 includes the washing step 502, the digesting step 504, the stopping digestion step 506, the centrifuging step 508 and the selectively removing pellet phase material step 510 as discussed with FIG. 19, but showing more detail for some processing alternatives for step 510. As shown in FIG. 20, the step 510 includes steps 511, 512 and 514. During the step 511, the lower-density material phases formed during centrifuging may be removed from the container while the pellet phase is retained within the container, preferably while maintaining the pellet phase in an undisturbed state, in place at the location of the container where the pellet collected during the centrifuging. The step 511 may include any or any combination of the features as discussed above. As shown in FIG. 20, after the removing lower-density phases step 511, the method includes a dispersing cells step 512. During the dispersing cells step 512, aqueous suspension liquid is introduced into the container to mix with the pellet phase and to act as a dispersion medium for dispersing cells of the pellet phase in the suspension liquid. Dispersion of cells from the pellet phase may be aided by tapping the container to dislodge and break up the pellet phase to assist effective dispersion of the leuko stromal vascular cells in the suspension liquid. The dispersing cells step 512 may include any of the features as discussed above. After the dispersing cells step 512, the processing shown in FIG. 20 includes a removing dispersed cells step 514, during which most, and preferably substantially all, of the suspension liquid with the dispersed cells from the pellet phase is removed from the container, thereby recovering the leuko stromal vascular cell from the container. The removing dispersed cells step 514 may include any of the features discussed above.

As an alternative to the processing for the selectively removing pellet phase material step 510 shown in FIG. 20, after the removing lower-density material phases step 511, the material of the pellet phase could be removed from the container by direct aspiration through an aspiration tube, such as a hypodermic needle. With this processing alternative, the cells of the pellet phase material would not be dispersed or suspended in a suspension liquid prior to removal from the container.

The foregoing discussion of the invention and different aspects thereof has been presented for purposes of illustration and description. The foregoing is not intended to limit the invention to only the form or forms specifically disclosed herein. Consequently, variations and modifications commensurate with the above teachings, and the skill or knowledge of the relevant art, are within the scope of the present invention. The embodiments described hereinabove are further intended to explain best modes known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art. Although the description of the invention has included description of one or more possible implementations and certain variations and modifications, other variations and modifications are within the scope of the invention, e.g., as may be within the skill and knowledge of those in the art after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. Furthermore, any feature described or claimed with respect to any disclosed implementation may be combined in any combination with one or more of any other features of any other implementation or implementations, to the extent that the features are not necessarily technically compatible, and all such combinations are within the scope of the present invention.

The terms "comprising", "containing", "including" and "having", and grammatical variations of those terms, are intended to be inclusive and nonlimiting in that the use of such terms indicates the presence of some condition or feature, but not to the exclusion of the presence also of any other condition or feature. The use of the terms "comprising", "containing", "including" and "having", and grammatical variations of those terms in referring to the presence of one or more components, subcomponents or materials, also include and is intended to disclose the more specific embodiments in which the term "comprising", "containing", "including" or "having" (or the variation of such term) as the case may be, is replaced by any of the narrower terms "consisting essentially of" or "consisting of" or "consisting of only" (or the appropriate grammatical variation of such narrower terms). For example, the a statement that some thing "comprises" a stated element or elements is also intended to include and disclose the more specific narrower embodiments of the thing "consisting essentially of" the stated element or elements, and the thing "consisting of" the stated element or elements. Examples of various features have been provided for purposes of illustration, and the terms "example", "for example" and the like indicate illustrative examples that are not limiting and are not to be construed or interpreted as limiting a feature or features to any particular example. The term "at least" followed by a number (e.g., "at least one") means that number or more than that number. The term at "at least a portion" means all or a portion that is less than all. The term "at least a part" means all or a part that is less than all.

What is claimed is:

1. An apparatus for processing human biological material containing stringy tissue, the apparatus comprising;
    a container having an internal containment volume, the internal containment volume including a tissue retention volume and a filtrate volume;
    a filter disposed within the internal containment volume with the tissue retention volume on one side of the filter and the filtrate volume on another side of the filter with the tissue retention volume and the filtrate volume being in fluid communication through the filter;
    an inlet port in fluid communication with the tissue retention volume and configured to access the tissue retention volume for introducing human biological material into the tissue retention volume;
    a suction port in fluid communication with the filtrate volume and configured to access the filtrate volume for suctioning material from the filtrate volume;
    a tissue collector disposed in the tissue retention volume and rotatable relative to the container in at least a first direction of rotation about an axis of rotation, the tissue collector including at least one toothed member that sweeps through a portion of the tissue retention volume when the tissue collector is rotated in the first direction, the toothed member being configured with a plurality of teeth to collect and retain stringy tissue when the tissue collector is rotated in the first direction in contact with human biological material containing stringy tissue disposed in the tissue retention volume; and
    wherein, each said toothed member has a first end located radially toward the axis and a second end located radially away from the axis, each said toothed member includes between the first end and the second end at least three teeth and an open space between the teeth of each pair of adjacent said teeth and the teeth project toward a leading side of the toothed member when the tissue collector is rotated in the first direction.

2. An apparatus according to claim 1, wherein each said toothed member includes at least 5 of said teeth.

3. An apparatus according to claim 1, wherein the tissue collector comprises at least two of said toothed member.

4. An apparatus according to claim 1, wherein the second end of each said toothed member is located from one to 10 centimeters from the axis.

5. An apparatus according to claim 1, wherein the teeth project in a plane of rotation of the toothed member when the tissue collector is rotated in the first direction.

6. An apparatus according to claim 1, wherein each of the teeth has a height of from 1 millimeter to 10 millimeters relative to a bottom of each adjacent said open space.

7. An apparatus according to claim 1, comprising a first mixing impeller in the tissue retention volume.

8. An apparatus according to claim 7, wherein the first mixing impeller is configured to direct axial flow from the first mixing impeller in a direction toward the tissue collector.

9. An apparatus according to claim 7, wherein the first mixing impeller includes at least one portion configured to scrape a portion of the filter when the first mixing impeller is operated.

10. An apparatus according to claim 9, wherein each said portion of the first mixing impeller configured to scrape a portion of the filter includes a peripheral edge portion of an impeller blade of the first mixing impeller.

11. An apparatus according to claim 9, wherein at least a part of each said portion of the filter is in a tapered portion of the filter that is disposed in a tapered portion of the internal containment volume.

12. An apparatus according to claim 7, wherein the tissue collector and the first mixing impeller are coaxial and rotatable about the axis in the first direction.

13. An apparatus according to claim 12, wherein a spacing along the axis between the first mixing impeller and the tissue collector is in a range of from 0.5 centimeter to 5 centimeters.

14. An apparatus according to claim 7, wherein the first mixing impeller extends to a first radial distance from the axis and the tissue collector extends to a second radial distance from the axis, wherein the second radial distance is larger than the first radial distance by at least 1 millimeter.

15. An apparatus according to claim 7, comprising a second mixing impeller in the tissue retention volume.

16. An apparatus according to claim 15, wherein the second mixing impeller is configured to direct axial flow in a direction away from the tissue collector when the mixing impeller is rotated about the axis in the first direction.

17. An apparatus according to claim 15, wherein the tissue collector and the second mixing impeller are coaxial and rotatable about the axis in the first direction.

18. An apparatus according to claim 17, wherein a spacing along the axis between the second mixing impeller and the tissue collector is in a range of from 0.5 centimeter to 5 centimeters.

19. An apparatus according to claim 15, wherein the second mixing impeller extends to a third radial distance from the axis that is at least 1 millimeter smaller than a radial distance from the axis to which the tissue collector extends.

20. An apparatus according to claim 1, wherein the apparatus is orientable in a first orientation in which the inlet port and the suction port are configured for access therethrough from above the container into the internal containment volume.

21. An apparatus according to claim 20, wherein in the first orientation, all access to the internal containment volume is from above the container.

22. An apparatus according to claim 20, comprising an extraction port configured for accessing the internal containment volume to remove processed biological material from the internal containment volume; and wherein the extraction port is configured for access therethrough from above the container into the internal containment volume when the apparatus is oriented in the first orientation.

23. An apparatus according to claim 22, wherein access through the extraction port is through a lumen extending through a rotatable shaft aligned with the axis.

24. An apparatus according to claim 22, wherein no access is provided into the internal containment volume through a lumen extending through a rotatable shaft.

25. An apparatus according to claim 1, wherein the filter has a separation size in a range of from 70 to 400 microns.

26. An apparatus according to claim 1, wherein the container is configured to be received in a centrifuge for centrifuging the container.

27. An apparatus according any to claim 1, wherein the internal containment volume has a volume in a range of from 100 cubic centimeters to 1300 cubic centimeters.

28. An apparatus according to claim 1, wherein:
the internal containment volume includes a pellet well disposed in a bottom portion of the filtrate volume below a bottom elevation of the filter and accessible only from above when the apparatus is in an access orientation;
the filtrate volume includes a lower tapered portion below a bottom elevation of the filter and above a top elevation of the pellet well;
the lower tapered portion of the filtrate volume is defined by internal wall surfaces of the container that are each inclined relative to horizontal at a maximum angle of no larger than 60° when the container is in the access orientation;
at least a portion of the pellet well is defined by a wall surface of the container inclined relative to horizontal at an angle that is larger than the maximum angle when the apparatus is in the access orientation.

29. An apparatus according to claim 28, wherein the filter has a separation size that is larger than 400 microns and not larger than 800 microns.

30. An apparatus according to claim 28, wherein the wall surface of the container defining at least a portion of the pellet well is inclined relative to horizontal at an angle of at least 70° when the apparatus is in the access orientation.

31. An apparatus according to claim 28, wherein:
when the apparatus is in the access orientation, the pellet well has at least one portion with a vertical length of 1 centimeter, a maximum horizontal dimension along the vertical length of no larger than 5 millimeters and a minimum horizontal dimension along the vertical length of no smaller than 1.5 millimeters.

32. An apparatus according to claim 28, wherein the pellet well has a volume in a range of from 0.5 cubic centimeter to 2 cubic centimeters.

33. An apparatus according to claim 28, wherein the internal containment volume has a volume in a range of from 150 cubic centimeters to 350 cubic centimeters.

34. A method of processing adipose tissue using an apparatus according to claim 1, the method comprising processing in the container of the apparatus, the processing comprising:
washing adipose tissue within the container to remove contaminants from the adipose tissue.

35. A method according to claim 34, comprising after the washing, removing washed adipose tissue from the container.

36. A method according to claim 34, comprising;
after the washing, digesting adipose tissue within the container, the digesting adipose tissue comprising adding to the container a volume of enzyme-containing digestion medium to contact washed adipose tissue in the container;
after permitting enzymatic digestion in the container for a retention time following adding the digestion medium, disposing the container in a centrifuge and centrifuging the container in the centrifuge to form density-separated phases within the container, the density-separated phases including lower-density material phases and a higher-density pellet phase comprising leuko stromal vascular cells; and
selectively removing material of the pellet phase from the container.

37. A method according to claim 36, wherein the selectively removing comprises:
inserting an aspiration tube from outside of to inside of the container to contact the pellet phase inside the container; and
aspirating at least a majority of material of the pellet phase through the aspiration tube to outside of the container without suspending material of the pellet phase in a suspension liquid in the container.

38. A method according to claim 37, wherein:
the lower-density material phases include an aqueous phase above the pellet phase; and
the aqueous phase is not removed from the container prior to the aspirating.

39. A method according to claim 37, wherein after the aspirating, the lower-density material phases remain in the container.

40. A method according to claim 37, wherein the inserting comprises inserting the aspiration tube downward into the container from above.

41. A method according to claim 37, wherein:
the aspirating comprises aspirating the at least a majority of the material of the pellet phase into a receptacle located outside of the container that is in fluid communication with the aspiration tube; and
prior to commencement of the aspirating, the receptacle contains a volume of dispersion medium and during the aspirating the dispersion medium mixes with the at least a majority of the material of the pellet phase in the receptacle.

42. A method according to claim 41, wherein the volume of the dispersion medium is in a range of from 2 times to 10 times a volume of the at least a majority of the material of the pellet phase that is aspirated into the receptacle during the aspirating.

43. A method according to claim 41, wherein during the aspirating the aspiration tube is in fluid communication with a syringe and the aspirating comprises collecting the at least a majority of the material of the pellet phase into the syringe.

44. A method according to claim 34, wherein:
the washing comprises multiple wash cycles with each said wash cycle comprises:
adding a volume of aqueous wash liquid to the container to contact the adipose tissue within the container;
mixing the wash liquid and the adipose tissue in the container; and
removing at least a majority of the wash liquid with contaminants from the filtrate volume of the container on a first side of the filter and retaining at least most of the adipose tissue in the tissue retention volume of the container disposed on a second side of the filter;
and the method further comprises:
after the washing, digesting adipose tissue within the container, the digesting adipose tissue comprising:

adding to the container a volume of digestion medium comprising a collagenase enzyme solution to contact washed adipose tissue in the container following the washing, wherein a volume ratio of the volume of digestion medium to volume of adipose tissue within the container is in a range of from 0.6:1 to 2:1 and where the digestion medium provides from 150 to 300 collagen digestion units (CDU) per milliliter of catalytic volume, wherein the catalytic volume is the total of the volume of digestion medium and the volume of adipose tissue within the container; and after the adding of the volume of digestion medium, permitting enzymatic digestion within the container for a retention time in a range of from 20 minutes to 50 minutes while the container is disposed in a temperature controlled environment maintained within a temperature range of from 32° C. to 38° C. and with at least occasional agitation of contents within the container; and not later than 50 minutes following the adding of the volume of digestion medium, adding a stopping reagent to the container to stop enzymatic activity within the container;

disposing the container in a centrifuge and centrifuging the container in the centrifuge to form density-separated phases within the container, the density-separated phases including lower-density material phases and a higher-density pellet phase comprising leuko stromal vascular cells;

after the centrifuging, removing the container from the centrifuge; and removing the lower-density material phases from the container while retaining the pellet phase within the container.

45. A method according to claim 34, wherein the washing comprises adding to the container a wash liquid at a temperature in a range of from 32° C. to 38° C.

* * * * *